(12) United States Patent
Chou et al.

(10) Patent No.: US 9,915,614 B2
(45) Date of Patent: Mar. 13, 2018

(54) MICROFLUIDIC SYSTEMS AND DEVICES FOR MOLECULAR CAPTURE, MANIPULATION, AND ANALYSIS

(71) Applicants: Academia Sinica, Taipei (TW); Max-Planck-Institut Für Eisenforschung GmbH, Düsseldorf (DE)

(72) Inventors: Chia-Fu Chou, Taipei (TW); Lesser-Rojas Leonardo, Taipei (TW); Ming-Lee Chu, Taipei (TW); Andreas Erbe, Düsseldorf (DE)

(73) Assignees: ACADEMIA SINICA, Taipei (TW); MAX-PLANCK-INSTITUT FUR EISENFORSCHUNG GMBH, Dusseldorf (DE)

( * ) Notice: Subject to any disclaimer, the term of this patent is extended or adjusted under 35 U.S.C. 154(b) by 19 days.

(21) Appl. No.: 13/872,013

(22) Filed: Apr. 26, 2013

(65) Prior Publication Data
US 2014/0320849 A1    Oct. 30, 2014

(51) Int. Cl.
*G01N 21/00* (2006.01)
*G01N 21/65* (2006.01)
*B03C 5/02* (2006.01)
*G01N 33/487* (2006.01)

(52) U.S. Cl.
CPC ........... *G01N 21/65* (2013.01); *B03C 5/026* (2013.01); *B03C 2201/26* (2013.01); *G01N 33/48721* (2013.01)

(58) Field of Classification Search
CPC ..... G01N 27/26; G01N 27/65; G01N 15/1434; G01N 1/4077
See application file for complete search history.

(56) References Cited

U.S. PATENT DOCUMENTS 4,236,256 A * 11/1980 Brackett et al. ............... 398/209
5,301,296 A *  4/1994 Mohri et al. .................. 711/128
(Continued)

OTHER PUBLICATIONS

S. "Gawad Micromachined impedance spectroscopy flow cytometer for cell analysis and particle sizing", Jul. 13, 2001.*
(Continued)

*Primary Examiner* — Michael A Lyons
*Assistant Examiner* — Maurice Smith
(74) *Attorney, Agent, or Firm* — Perkins Coie LLP

(57) ABSTRACT

Methods, systems, and devices are disclosed for molecular capture, manipulation, and analysis. In one aspect, a device to aggregate and characterize particles in a fluid includes an electrically insulative substrate including a channel to carry an electrically conducting fluid containing particles, electrodes located in the channel forming a nanoscale opening and including an insulating layer over their surface at the opening, a first circuit to apply a non-uniform ac electric field and a dc bias signal across the electrodes, in which the applied non-uniform ac electric field produces a positive dielectrophoretic force to aggregate the particles in a trapping region including the opening and adjacent region, a second circuit to detect changes in a dc current caused by at least some of the particles in the trapping region, and an optical device that directs a coherent light beam on the opening to determine Raman spectra of the particles in the trapping region.

36 Claims, 14 Drawing Sheets

(56) References Cited

U.S. PATENT DOCUMENTS

| | | | |
|---|---|---|---|
| 6,437,551 B1* | 8/2002 | Krulevitch et al. | 324/71.1 |
| 6,627,067 B1* | 9/2003 | Branton | B24B 37/013 204/403.06 |
| 6,744,245 B2* | 6/2004 | Taylor et al. | 324/71.4 |
| 7,341,841 B2* | 3/2008 | Metzger et al. | 435/7.2 |
| 2003/0119057 A1* | 6/2003 | Gascoyne et al. | 435/7.1 |
| 2006/0246497 A1* | 11/2006 | Huang et al. | 435/6 |
| 2007/0134866 A1* | 6/2007 | Huang et al. | 438/199 |
| 2007/0241748 A1* | 10/2007 | Ghallab et al. | 324/260 |
| 2009/0023146 A1* | 1/2009 | Harnack | B01L 3/502761 435/6.12 |
| 2009/0166222 A1 | 7/2009 | Mirkin et al. | |
| 2010/0156444 A1* | 6/2010 | Ponjee et al. | 324/703 |
| 2011/0031389 A1* | 2/2011 | Reed et al. | 250/282 |
| 2011/0056845 A1* | 3/2011 | Stellacci et al. | 205/777.5 |
| 2012/0046883 A1* | 2/2012 | Ayliffe et al. | 702/26 |

OTHER PUBLICATIONS

Shih-Mo Yang. "Dynamic Pico-Liter Bubble Manipulation Via Tiopc-Based Light-Induced Dielectrophoresis", 2010.*

Divya Padmaraj,"Nanogap Capacitors Used for Impedance Characterization of Living Cells", 2007.*

David Holmes, "High throughput particle analysis: Combining dielectrophoretic particle focusing with confocal optical detection", Dec. 5, 2005.*

Castle, Patrick, "Interfacial Scattering at Electrochemically Fabricated Atom-Scale Junctions between Thin Gold Film Electrodes in a Microfluidic Channel", Analytical Chemistry, vol. 77, No. 1, Jan. 1, 2005.*

Rokadia, Husein,"Characterization of Laterally Aligned Carbon Nanotubes Formed by AC Dielectrophoresis" IEEE, Aug. 2, 2007.*

Holzel, R., et al., "Trapping single molecules by dielectrophoresis," Physical Review Letters, 95:128102-1-4, Sep. 2005.

Osberg, K.D., et al., "Dispersible gold nanorod dimers with sub-5 nm gaps as local amplifiers for surface-enhanced raman scattering," Nano Letters, 12:3828-3832, Jun. 2012.

Ward, D.R., et al., "Electromigrated nanoscale gaps for surface-enhanced raman spectroscopy," Nano Letters, 7(5):1396-1400, Apr. 2007.

Zheng, G., et al., "Complementary electrical and spectroscopic detection assays with on-wire-lithography-based nanostructures," Small, 5(9):2537-2540, Aug. 2009.

Zheng, G., et al., "Spectroscopically enhancing electrical nanotraps," Angew. Chem. Int. Ed., 47:1938-1941, Jan. 2008.

* cited by examiner

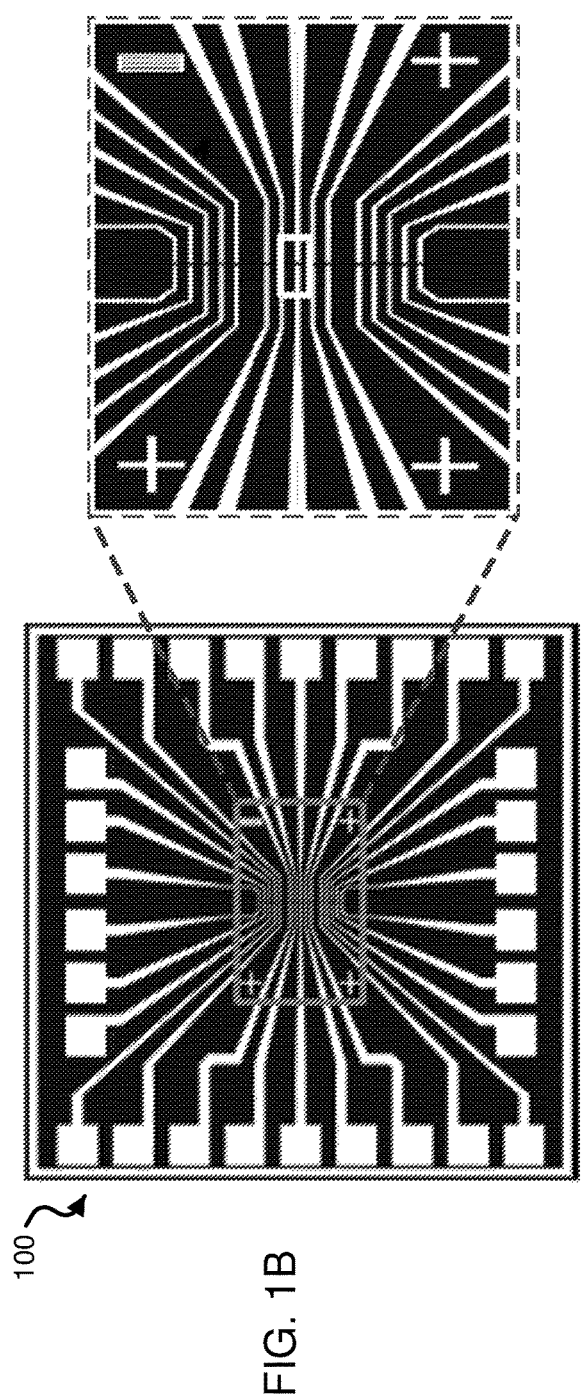
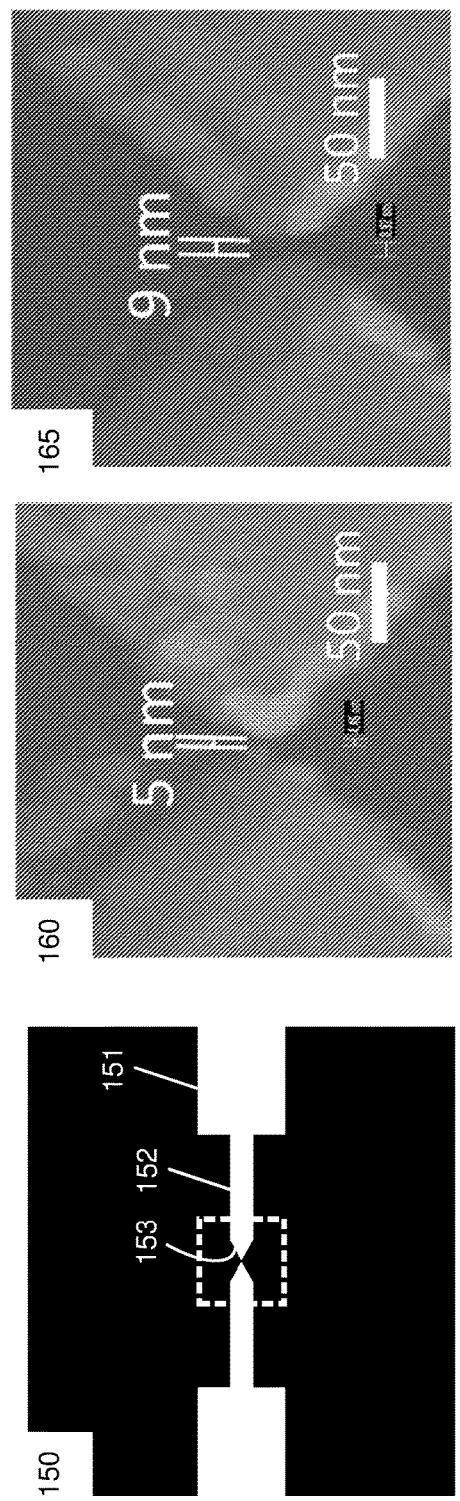
FIG. 1B
FIG. 1C
FIG. 1D
FIG. 1E

MICROFLUIDIC SYSTEMS AND DEVICES FOR MOLECULAR CAPTURE, MANIPULATION, AND ANALYSIS

CROSS REFERENCE TO RELATED APPLICATIONS

This patent document claims the benefit of priority of Taiwan Patent Application No. 101139419, filed on Oct. 25, 2012. The entire content of the before-mentioned patent application is incorporated by reference as part of the disclosure of this application.

TECHNICAL FIELD

This patent document relates to biological sensors and analytical devices.

BACKGROUND

A biological sensor or biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, aptamers, peptides, nucleic acids, etc., or small molecules such as carbohydrates, as well as virus and living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by a suitable transduction mechanism, for example, electrical, magnetic, mechanical, physicochemical, electrochemical, optical, piezoelectric, or others.

SUMMARY

Techniques, systems, and devices are described for detecting small molecules by using microfluidic systems having multifunctional nano-sized structures to provide dielectrophoretic trapping without pre-concentration of the target molecules and to simultaneously analyze the captured molecules using surface enhanced Raman spectroscopy.

In one aspect of the disclosed technology, a device to aggregate and characterize particles in a fluid includes a substrate that is electrically insulating, a channel formed of an electrically insulative material on the substrate and structured to carry an electrically conducting fluid containing particles, a first electrode and a second electrode formed of an electrically conductive material and located in the channel to form an opening with a size in the nanometer range, the first and second electrodes including an electrically insulating layer over the electrode surface at the opening, a first circuit electrically coupled to the first and second electrodes to apply a non-uniform ac electric field and a dc bias signal across the first and second electrode, wherein the applied non-uniform ac electric field produces a positive dielectrophoretic force ($F_{PDEP}$) in a direction towards the opening to aggregate the particles in a trapping region including the opening and in a region adjacent to the opening, a second circuit coupled to the first and second electrodes to detect changes in a dc current produced by the applied dc bias signal caused by at least some of the particles in the trapping region, and an optical device that directs a coherent light beam on the opening and detects inelastic scattering of the light beam by at least some of the particles in the trapping region to determine their Raman spectra.

Implementations of the device can optionally include one or more of the following features. For example, the first and second electrodes can be structured to extend into the channel such that the electrodes narrow a channel dimension. For example, the electrically insulative material can include at least one of glass, silica, oxidized silicon, silicon nitride, polysilsesquioxane (PSQ), polymethylmethacrylate (PMMA), or plastic. For example, the particles can include at least one of proteins, nucleic acids, peptides, carbohydrates, or nanoparticles. For example, the size of the opening can be configured in a range of 1 to 10 nanometers. In some implementations of the device, for example, the electrically insulating layer can include a native metal oxide coating, e.g., in which the native metal oxide coating includes titanium oxide (e.g., which can be configured to have a thickness of 0.1 to 2 nanometers). In some implementations of the device, for example, the electrically insulating layer can be formed of a self-assembled monolayer. In some implementations of the device, for example, the optical device can be configured to detect an illumination intensity of the aggregated particles, e.g., such as fluorescence. In some implementations, for example, the device also can include a sensor or sensors located along the channel to detect a parameter of the aggregated particles, e.g., the sensor(s) being an electrical sensor, an electrochemical sensor, a mechanical sensor, and/or a magnetic sensor. In some implementations of the device, for example, the second circuit can include a transimpedance amplifier.

In another aspect, a method to aggregate and characterize particles in a fluid includes receiving an electrically conducting fluid containing particles in a channel formed of an electrically insulative material and having a pair of electrodes to form an opening at an interface between the electrodes with a size in the nanometer range, the electrodes including an electrically insulating layer over the electrode surface at the opening, selecting a frequency and magnitude of an ac electric field and a bias magnitude of a dc electrical signal to be applied across the electrodes, applying the ac electric field to aggregate the particles in a trapping region including the opening and in a region adjacent to the opening, and applying the dc electric signal across the electrodes to measure a current produced based on the presence of the particles in the trapping region.

Implementations of the method can optionally include one or more of the following features. In some implementations of the method, for example, the particles include a first type of particles and a second type of particles, and the method can also include selecting electrical parameters to separate the first type of particles from the second type of particles based on differences in polarizability and electrokinetic mobility of the first and second type of particles. For example, the method can also include controlling the duration of the applied ac electric field to temporally control the separation of the first and second type of particles. In some implementations, for example, the method can also include directing a coherent light beam on the opening, detecting, using an optical device, inelastic scattering of the light beam by at least some of the particles aggregated in the trapping region, and determining a Raman spectra from the detected light.

In another aspect, a method to aggregate and characterize particles in a fluid includes receiving an electrically conducting fluid containing particles in a channel formed of an electrically insulative material and having a pair of electrodes to form an opening at an interface between the electrodes with a size in the nanometer range, the electrodes including an electrically insulating layer over the electrode surface at the opening, selecting a frequency and magnitude of an ac electric field to be applied across the electrodes, applying the ac electric field to aggregate the particles in a trapping region including the opening and in a region adjacent to the opening, directing a coherent light beam on the opening, detecting, using an optical device, inelastic scattering of the light beam by at least some of the particles aggregated in the trapping region, and determining a Raman spectra from the detected light.

Implementations of the method can optionally include one or more of the following features. In some implementations of the method, for example, the particles include a first type of particles and a second type of particles, and the method can also include selecting electrical parameters to separate the first type of particles from the second type of particles based on differences in polarizability and electrokinetic mobility of the first and second type of particles. For example, the method can also include controlling the duration of the applied ac electric field to temporally control the separation of the first and second type of particles. In some implementations, for example, the method can also include selecting a bias magnitude of a dc electrical signal to be applied across the electrodes, and applying the dc electric signal across the electrodes to measure a current produced based on the presence of the particles in the trapping region.

In another aspect, a system to characterize particles includes an electrode dielectrophoresis chip, including: (i) a substrate that is electrically insulating and structured to define a channel to carry an electrically conducting fluid containing particles, and (ii) an array of paired electrodes formed of an electrically conductive material and located in the channel to form an opening with a size in the nanometer range, wherein electrodes in at least one electrode pair of the array are structured to include an electrically insulating layer over the electrode surface at the opening; an electrical energy source electrically coupled to the electrode dielectrophoresis chip to generate a non-uniform ac electric field and a dc bias signal across the paired electrodes, wherein the non-uniform ac electric field produces a positive dielectrophoretic force ($F_{PDEP}$) in a direction towards the opening to aggregate the particles in a trapping region including the opening and in a region adjacent to the opening; a circuit board including an electrical circuit coupled to the first and second electrodes and configured to detect changes in a dc current produced by the applied dc bias signal caused by at least some of the particles aggregated in the trapping region, the circuit board providing a base to attach the electrode dielectrophoresis chip and electrically couple the electrode dielectrophoresis chip to the electrical circuit; an optical device that directs a coherent light beam on the opening and detects inelastic scattering of the light beam by at least some of the particles aggregated in the trapping region; and a processing unit to process at least one of the detected light to determine their Raman spectra or the detected dc current as data to determine a characteristic of the particles.

Implementations of the system can optionally include one or more of the following features. In some implementations of the system, for example, the processing unit can be configured on the circuit board. For example, the circuit board can further include a memory unit coupled to the processing unit to store the data. For example, the circuit board can further include an input/output unit to send at least one of the data, the detected dc current signals, or the Raman spectra data.

The subject matter described in this patent document can be implemented in specific ways that provide one or more of the following features. For example, the disclosed technology can include nanoelectrode structures to provide dielectrophoresis-enabled molecular capture and Raman spectroscopy characterization of individual and small populations of biomolecules with simultaneous real-time electronic monitoring. The disclosed technology can be particularly suitable for analysis and characterization for low-abundance biomolecules and nanomaterials. For example, the disclosed technology can be implemented for protein capture, e.g., in which efficient surface-enhanced Raman signals are utilized for molecular trapping right at the surface enhanced Raman spectroscopy (SERS) hotspot. The disclosed technology can be implemented with simultaneous electrical measurement, and any biosensing elements can be functionalized at the nanogap.

BRIEF DESCRIPTION OF THE DRAWINGS

FIGS. 1A-1K show schematics and images of an exemplary particle analysis platform of the disclosed technology including an exemplary microchip having the nanogap electrode array for particle trapping and characterization.

DETAILED DESCRIPTION

Figure 1A:
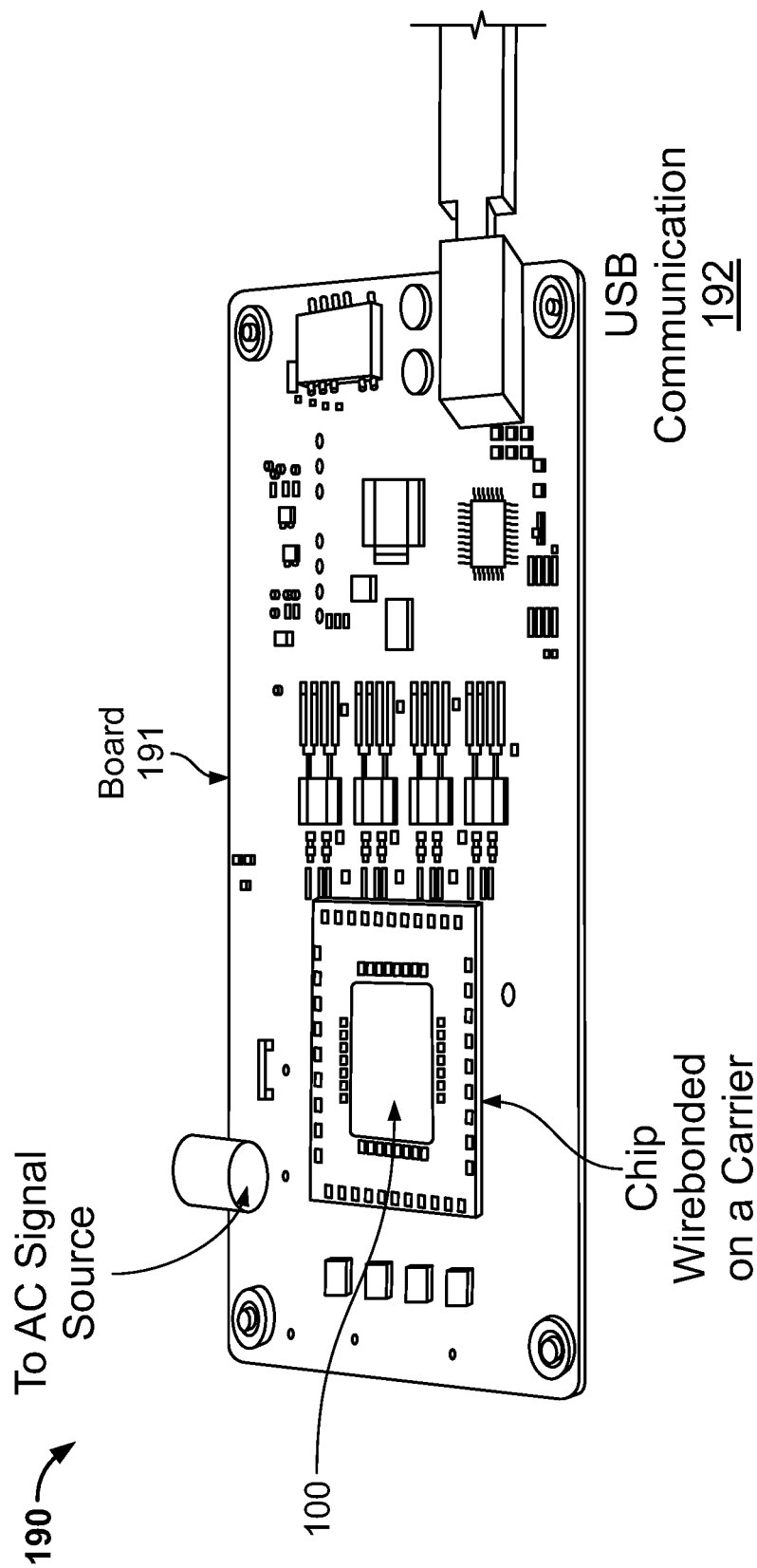

It is technically challenging to sense low numbers of biomarker proteins against a background of high concentration of other matrix proteins within physiologically relevant media. One way of achieving effective sensing is based on selective preconcentration of the biomarker proteins in the proximity of the sensor to increase local concentration of the target sample for sensing by the sensor. Various preconcentration methods are available but many such methods are limited in their performance. For example, chemical methods based on antibody depletion are unable to achieve the necessary degree of preconcentration of biomarker proteins, e.g., as such biomarkers are present at $10^6$-$10^{12}$-fold lower levels than the background proteins in blood. Other examples include the use of electrokinetic methods for selective preconcentration of biomolecules. One such electrokinetic method includes dielectrophoresis, which can enable selective trapping of biomolecules and bioparticles based on the characteristic frequency response of the dielectric permittivity of the biomolecule/particle versus that of the medium. Dielectrophoretic techniques have been shown to be effective in the sorting of somewhat similar sized biological cells with differing dielectric frequency response. However, its application to smaller sized biomarkers, e.g., such as nanoscale proteins and fragments of single-stranded deoxyribonucleic acid (ssDNA), have been ineffective so far.

Dielectrophoresis (DEP) is an electrokinetic phenomenon in which a force is exerted on a dielectric particle (e.g., polarizable particle, including molecules and nanoscale particles) in a suspending medium when the particle is subjected to a non-uniform electric field. Dielectrophoresis can be used to attract and separate various particles in aqueous media, depending on the dielectric response of the particle in the presence of the non-uniform electric field. Although particles in general can exhibit dielectrophoretic activity in the presence of an electric field, the magnitude of the dielectrophoretic force depends on the type of medium, certain properties of specific particles, e.g., electrical properties and shape and size, and the frequency of the electric field exerted on the particles. For example, tuning the electric field to particular frequencies can manipulate particles with a degree of selectivity, e.g., which can result in orientation, transportation, and/or separation of the particles in the medium. For example, the non-uniform electric field can create regions within the medium of greater and lesser electric field magnitudes that can steer the particles. For example, when the permittivity of the medium is greater than that of the particle, the particle moves to regions of lesser electric field strength within the medium. Alternatively, for example, when the particle's permittivity exceeds that of the medium, the particle moves to regions of stronger electric field strength.

The dielectrophoretic force (e.g., a translational force) can be represented as:

$$F_{DEP} = 2\pi r^3 \in_m Re[K(\omega)] \nabla E^2 \quad (1)$$

where r is the radius of the particle, $\in_m$ is the absolute permittivity of the suspending medium, E is the amplitude of the applied field (e.g., root-mean-squared E in the case for an AC field), and $Re[K(\omega)]$ represents the real part of the Clausius-Mossotti (CM) factor, which can be represented by:

$$K(\omega) = (\in_p^* - \in_m^*)/(\in_p^* + 2\in_m^*) \quad (2)$$

where $\in_m^*$ and $\in_p^*$ are the complex permittivities of the medium and particle respectively, and $(\in^* = \in - j\sigma/\omega)$, in which $\sigma$ is the conductivity, $\in$ is the permittivity, and $\omega$ is the angular frequency. The CM factor represents the frequency-dependent dielectric contrast between the particle and the suspending medium in an external driving field. The CM factor determines if the particle transport is either towards (attracted) the high field gradient region of the fluidic channel (e.g., when $Re[K(\omega)]>0$), correspondingly by positive dielectrophoresis (PDEP), or if the particle transport is away (repelled) from the high field gradient region of the fluidic channel (e.g., when $Re[K(\omega)]<0$), correspondingly by negative dielectrophoresis (NDEP).

The force $F_{DEP}$ increases with the size of the molecules ($\sim r^3$). Therefore, it can be difficult in various applications to generate a sufficient dielectrophoretic force to enrich small biomolecules such as proteins by DEP (e.g., proteins can be a few nanometers in size, in the 10's-100 kDa). Also, proteins tend to exhibit a small CM factor due to their low polarizability. To overcome this limitation and entrap and enrich small biomolecules, the disclosed technology creates a highly focused field and field gradient to increase $F_{DEP}$ by engineering the $\nabla E^2$ (or $E \cdot \nabla E$) term in Eq. (1).

DEP has been successfully used to manipulate bioparticles such as DNA, RNA, proteins, viruses and bacterial spores, and provide means for rapid enrichment and mass transport of proteins. In some examples, DEP can be applied to manipulate bioparticles for enrichment and/or mass transport using electrodeless DEP, insulator-based DEP, or metal electrode-based DEP modalities. In metal electrode-based DEP (MDEP), the DEP field is generated by applying a voltage across metal electrodes.

Raman spectroscopy is a quantitative and nondestructive optical technique based on inelastic scattering of photons by molecular vibrations of materials (e.g., such as biopolymers) that is capable of detecting information on the biochemical composition of cells (e.g., amino acids and proteins, lipids, and nucleic acids, among others. For example, Raman spectroscopy can be used as a bio-characterization and analysis tool to study cellular events, e.g., such as chemical changes and cell death induced by drugs or toxins, as well as cellular changes at different time points in the cell cycle. Raman spectroscopy can provide data related to physiological processes occurring within a cell without the use of chemical tags, leaving cellular functions unaltered during observations and available for repeated monitoring of time-dependent events of the same cell.

Techniques, systems, and devices are described for detecting small molecules by using microfluidic systems having multifunctional nano-sized structures to provide dielectrophoretic trapping without pre-concentration of the target molecules and to simultaneously analyze the captured molecules using surface enhanced Raman spectroscopy.

In one aspect, a device to aggregate and characterize particles in a fluid includes a substrate that is electrically insulating, a channel formed of an electrically insulative material on the substrate and structured to carry an electrically conducting fluid containing particles, a first and second electrode formed of an electrically conductive material and located in the channel to form an opening with a size in the nanometer range, in which the first and second electrodes include an electrically insulating layer over at least a portion of the electrode surface at the opening, a first circuit electrically coupled to the first and second electrodes to apply a non-uniform ac electric field and a dc bias electric field across the first and second electrode, in which the applied non-uniform ac electric field produces a positive dielectrophoretic force ($F_{PDEP}$) in a direction towards the opening to aggregate the particles in a trapping region including the opening and in a region adjacent to the opening, a second circuit coupled to the first and second electrodes to detect changes in a DC current produced by the applied dc bias electric field caused by at least some of the particles in the trapping region, and an optical device to direct a coherent light beam on the opening and detect inelastic scattering of the light beam by at least some of the particles in the trapping region to determine their Raman spectra. In some implementations of the device, for example, the first and second electrodes can be configured to extend into the channel such that the electrodes narrow a channel dimension. In some implementations, the first and second electrodes can include a native metal oxide coating on at least the interfacing regions (e.g., electrode tips) of the electrodes. For example, the native metal oxide coating can provide a layer that reduces electrochemical reactions, e.g., which can lead to corrosion of the electrodes. In some implementations, the first and second electrodes can include gold, e.g., in which the electrodes include a gold surface chemically modified with an electrically insulating self-assembled monolayer.

In some aspects, the disclosed technology includes a versatile nano-electronic platform for the manipulation (e.g., trapping) and sensing of particles including, for example, biological molecules (e.g., such as proteins) and solid state nanomaterials (such as carbon nanotubes) based on electrode nanogaps, which function as dielectrophoresis-enabled particle trapping templates and multifunctional Raman spectroscopic and nanoelectronic detection substrates. The nano-sized gaps between the electrodes are able to act as an effective plasmonic antenna that produce surface-enhanced Raman spectroscopy effects of the target particles in the junctions. During the particle trapping process, current measurements across the nanoelectrodes can be used to detect the presence of trapped protein(s) in the nanogap. Concurrent recording of time-dependent Raman spectra and electrical signatures provide direct evidence of biomolecules or nanomaterials appearing in the nanogap.

In some embodiments, the disclosed nanoconstrictions can be configured as metallic electrodes forming nano-sized gaps between them. For example, in some implementations, ac and dc electric fields are applied across the nanostructure electrodes in aqueous solutions to generate a non-uniform electric field that exerts forces on polarizable dielectric particles via dielectrophoresis. Dielectrophoretic forces attract particles across the inter-electrode space thus permitting the observation of trapping down to the single molecule or few molecules level. Thus, for example, the metallic nanostructures of the disclosed devices and systems can simultaneously manipulate and capture freely diffusing proteins or other small molecules present in the aqueous solution and characterize the captured molecules both spectroscopically and electronically in real-time.

In some aspects, the disclosed technology includes a versatile particle analysis platform based on a nanogap electrode that can be used for the manipulation and sensing of macromolecules. Exemplary implementations of the disclosed molecular analysis is described demonstrating low-copy number protein analysis. In some implementations, the particle analysis platform includes an array of Ti nanogap electrodes with a sub-10 nm gap size that function as AC dielectrophoresis-based molecular trapping structures, "hotspots" for surface plasmon enhanced Raman spectroscopy as well as fluorescence imaging, and tunneling current readers. For example, during molecular trapping, current measurements across the nanogaps and recorded Raman spectra show the presence and characteristics of the trapped particles (e.g., proteins), including showing their presence and characteristics on a single-particle/molecule level. Such identification and analysis can also, for example, be indicated by the discrete jumps in current signals. The disclosed particle analysis platform is thus capable of low-concentration heterogeneous sample analysis without the need for target preconcentration.

Detection of proteins present as less than 1,000 molecules in a solution is challenging, as this abundance is far below the sensitivity of conventional protein analysis methods, such as enzyme-linked immunosorbent assays. Detection and analysis of low-copy-number biological specimens down to the single- or few-molecule level can be possible due to capabilities offered through a variety of technologies, including micro- and nano-fluidics, nanopore technologies, molecular electronics, single-molecule fluorescence, as well as surface-enhanced Raman spectroscopy (SERS) and tip-enhanced Raman spectroscopy (TERS). Combinations of multiple functionalities and detection strategies of such technologies have been employed to achieve fast and reliable label-free analysis of heterogeneous targets at ultralow concentrations. However, the overall sensitivity and/or detection efficiency have shown to be limited by diffusive analyte transport to the actual sensing element. The disclosed technology addresses such limitations and provides for the directed transport of few sample molecules to sensing elements, to enable detection on practical time scales.

In some embodiments, the disclosed particle analysis platform includes metal electrodes configured to form nanoscale gaps between two electrode tips, referred to in this patent document as nanogap electrodes or electrode nanogaps. The exemplary nanogap electrodes described herein can provide multifunctional advantages such as acting as an analytical device and a molecular trapping device at the same time. For example, analytic signals can be optical and/or electronic. Also, for example, Raman scattering can be strongly enhanced for molecules at such metal nanogaps due to the confinement of electromagnetic waves near corners, edges and in the gaps, e.g., enabling the detection of a low number (e.g., less than 1,000) of molecules in the Raman hotspot. Additionally, measurements of currents (e.g., tunneling currents) across the nanometer-sized gaps can be used to identify single molecules present in the gaps. The disclosed technology includes substantially narrow distances of the nanogap regions, leading to stronger electrode-molecule electronic coupling and an accompanying rise in current exhibited by the disclosed particle analysis platform. The disclosed particle analysis platform implements dielectrophoresis generated from the nanoelectrode for the trapping of molecular species and overcomes diffusive analyte transport.

The exemplary array of nanogaps of the disclosed particle analysis platform can use a material with a native oxide film, such as titanium, to provide the multifunctional manipulation (e.g., molecular trapping) and interrogation (e.g., optical and electrical characterization) of particles introduced in the system. For example, the use of a titanium oxide nanoelectrode structure limits nanoelectrode degradation. For example, gold, which is used in many existing SERS devices, can be prone to corrosion especially in chloride-containing electrolytes, which include almost all biologically relevant buffers. Also for example, aluminum can be prone to dissolution in acids. The exemplary array of nanogap electrodes can be fabricated to form gaps with widths less than 10 nm to capture freely diffusing protein molecules present in an aqueous solution using high-frequency DEP. Captured particles (e.g., biomolecules including proteins) can be detected in real time using the disclosed platform via SERS and/or by the current measurement across the nanogap. For example, the use of higher AC frequencies to obtain DEP trapping avoids effects based on solvent flow and relies exclusively on the polarizability contrast between the analyte and the solvent, thus making the trapping reversible and the detection many orders of magnitude faster than conventional methods. The combination of electronic and Raman spectroscopic detection of the DEP-captured molecules makes the platform an attractive label-free bioanalytical tool.

FIGS. 1A-1K show schematics and images of an exemplary particle analysis platform of the disclosed technology including an exemplary microchip having the nanogap electrode array for particle trapping and characterization.

FIG. 1A shows an image of a particle analysis system 190 that includes a particle trapping and characterization chip 100 configured on a chip carrier (e.g., electrically coupled via wire bonding) connected to a circuit board 191 of the system 190 and in electrical communication with various components of the system 190 on the circuit board 191 including, for example, signal processing components and systems, memory, power sources, and/or communication systems, e.g., such as a Universal Serial Bus (USB) communication port or unit 192. The circuit board 191 can be operated to control and modulate applied AC and DC signals for DEP trapping, amplify and/or filter acquired signals (e.g., such as DC current changes across electrode terminals), and store and/or output raw or processed data.

In some implementations, the system 190 can include a processing unit such as a central processor unit and/or microcontroller that can be in communication with an input/output (I/O) unit, an output unit, and a memory unit. To support various functions of the processing unit, the exemplary processor can be included to interface with and control operations of other components of the system 190, such as the exemplary I/O unit, the exemplary output unit, and the exemplary memory unit. In some examples, the processing unit can be configured on the circuit board 191, while in other examples, the processing unit can be implemented as one of various data processing systems, such as a personal computer (PC), laptop, tablet, and mobile communication device. For example, the circuit board 191 can be configured to be operated remotely by a computer or other control system that communicates with the circuit board 191 to retrieve electronic data, e.g., in which individual data channels can be operated independently or in tandem.

To support various functions of the system 190, the exemplary memory unit can store other information and data, such as instructions, software, values, images, and other data processed or referenced by the processor. Various types of Random Access Memory (RAM) devices, Read Only Memory (ROM) devices, Flash Memory devices, and other suitable storage media can be used to implement storage functions of the memory unit. The exemplary memory unit can store data and information acquired by the chip 100, which can include current data and SERS data, system component parameters, data processing parameters, and processed parameters and data that can be used in the implementation of an RSI characterization. The memory unit can store data and information that can be used to implement the particle manipulation and characterization multi-functions of the system 190.

To support various functions of the system 190, the exemplary I/O unit can be connected to an external interface, source of data storage, or display device. Various types of wired or wireless interfaces compatible with typical data communication standards, such as the USB communication unit 192, IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, among other communication technologies, can be used to implement the I/O unit. The I/O unit can interface with an external interface, source of data storage, or display device to retrieve and transfer data and information that can be processed by the processor, stored in the memory unit, or exhibited on the output unit.

FIG. 1B shows a schematic of the chip 100 including the exemplary nanogap electrode array. In some implementations, for example, the chip 100 can be configured as a 7×7 mm$^2$ silicon-based chip with a 1.2 μm thick top layer of thermally grown $SiO_2$ on which the exemplary nanogap electrode pair structures branching from 15 parallel trapping microelectrode wires (microwires) coupled with contact pads are defined, e.g., using standard photolithography, thermal evaporation of Ti/Au and lift-off process (described in an exemplary fabrication method below). For example, the contact pads of the chip 100 provide for wire bonding interconnections to a printed circuit board, e.g., such as the circuit board 191, for electric field application, current amplification and/or data acquisition. FIG. 1B also shows an inset schematic providing a magnified view of the exemplary trapping microelectrode pairs of the chip 100.

FIG. 1C shows a diagram of an exemplary nanogap electrode pair structures 150 of the chip 100. The diagram of FIG. 1C shows electrically conductive conduits 151, e.g., which can be configured to be micrometers wide, branching into smaller electrically conductive conduits 152, e.g., which can be configured to be nanometers wide. For example, the smaller electrically conductive conduits 152 can be configured to have a 200 nm width. The smaller electrically conductive conduits 152 include metal oxide coated nanoelectrode tips 153 that interface with their respective counterpart to form a nanogap, e.g., which can be configured to be one to 10 nm apart, in which particles can be trapped when implementing the system 190.

FIGS. 1D and 1E show scanning electrode micrograph (SEM) images 160 and 165 showing inter-electrode nanogap region of a nanogap electrode pair having a 5 nm gap, as shown in the image 160, and a 9 nm gap, as shown in the image 165.

Figure 1F:
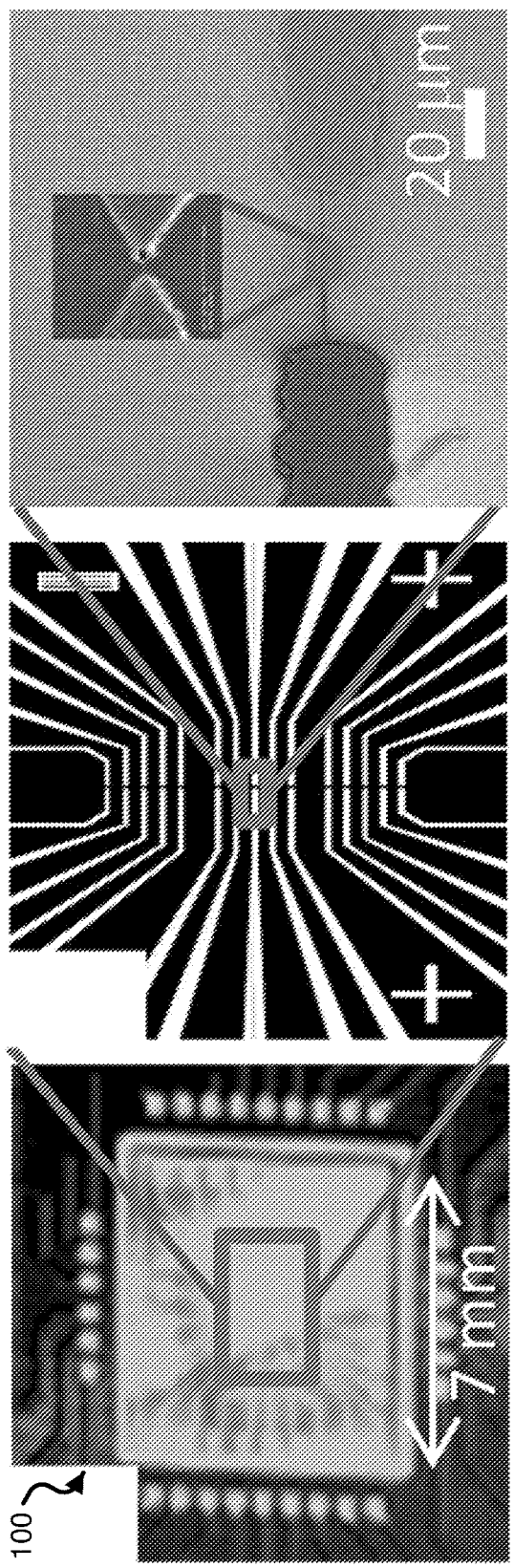

FIG. 1F shows an image series of the chip 100 including an optical image of the overall chip 100 (e.g., configured in the chip carrier of the system 190), a schematic diagram of the particle trapping and characterization region of the chip 100 formed by the nanogap electrode pairs, and SEM images of a nanogap electrode pair forming the nanogap region. As shown in the SEM images, the exemplary nanogap electrodes are configured as to be 200 nm wide and include a 40 nm Ti thin layer leading to an inter-electrode nanogap that can be defined of different sizes, e.g., such as substantially 5 nm as shown in FIG. 1D or 9 nm as shown in FIG. 1E.

Figure 1G:
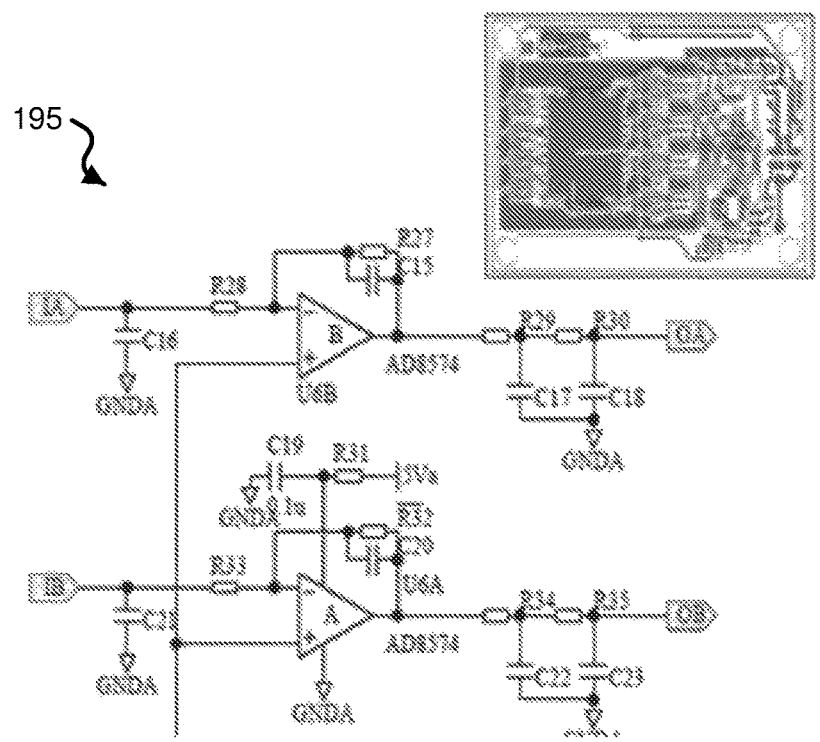

FIG. 1G shows a diagram of an exemplary transimpedance amplifier 195 with a low-pass filter for signal processing of acquired electrical signals from the nanogap electrodes 150, which can be included on the circuit board 191. For example, the transimpedance amplifier 195 can be used for current-to-voltage conversion. For example, the circuit board 191 can include a simultaneous multichannel current measurement amplifier, which can be in electrical communication with the transimpedance amplifier 195.

Figure 1H:
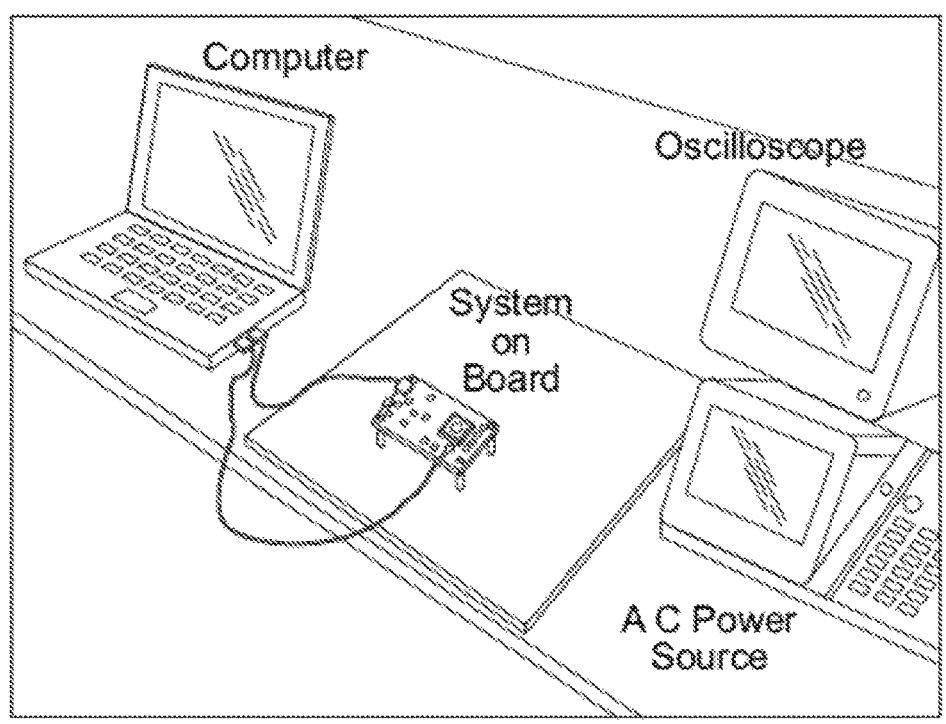

FIG. 1H shows an image of an exemplary set-up of the system 190 including a remote computing system to electrically interface with the circuit board 191 for one or more of control, data processing, data storage, and/or data display. The image shows an oscilloscope used to provide AC power to the system 190 through a power source port on the circuit board 191.

Figure 1I:
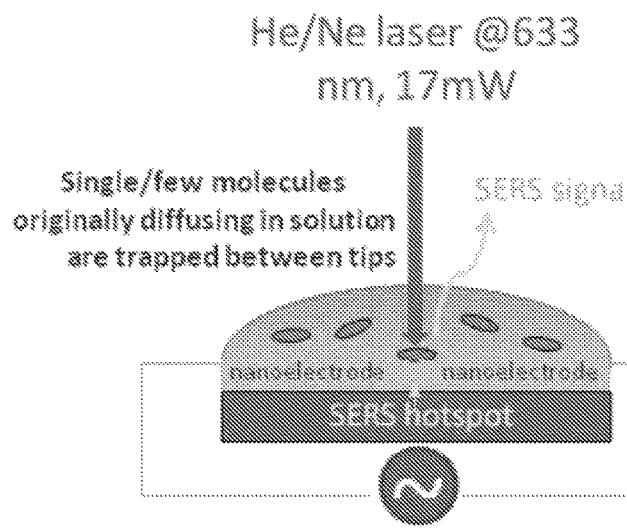

FIG. 1I shows an illustration of a generated SERS hotspot in the exemplary nanogap region of the chip 100, e.g., formed by the nanogap electrode pair structures 150, during operation of the system 190. For example, DEP-trapped particles by the nanogap electrode pair structures 150 can be scanned using confocal Raman spectroscopy with a coherent light source (e.g., such as He/Ne 633 nm laser excitation) shined on the metal oxide coated nanoelectrode tips 153. The nanoelectrode tips 153 can include free electrons on their surface that enhances the detectable Raman signal generating a SERS hotspot in the inter-electrode region and enabling detection of trapped particles, e.g., with single-particle to few-particle resolution.

Figure 1J:
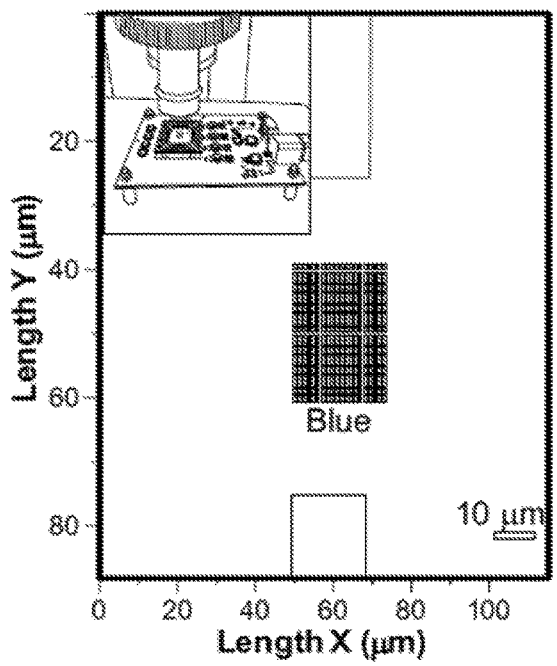

FIG. 1J shows an image of the inter-electrode nanogap region between the nanoelectrode tips showing the location of a SERS hotspot (blue region) on the chip 100 produced by a confocal Raman spectroscopy microscope laser light source. FIG. 1J includes an inset photograph of the board 191 under the confocal Raman spectroscopy microscope lens.

Figure 1K:
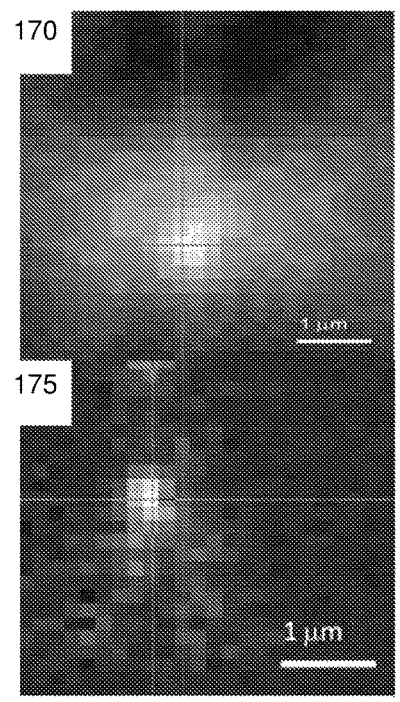

FIG. 1K shows fluorescent images 170 and 175 showing SERS hotspots located in the inter-electrode nanogaps of the nanoelectrode tips due to inelastic electronic effects in the electrodes. For example, the image 170 shows detected Si fluorescent peaks, e.g., integrated between 500 cm$^{-1}$ and 550 cm$^{-1}$, in which the position of the highest intensity corresponds to the nanogap region having the shined laser beam on the Si-based substrate. For example, the image 175 shows detected paraffin SERS signal in the inter-electrode region, e.g., integrated from 1450 cm$^{-1}$ to 1510 cm$^{-1}$, based on CH$_2$ bending mode (e.g., 1460 cm$^{-1}$) of paraffin.

The chip 100 can be fabricated using the following exemplary fabrication protocol. On the substrate of the disclosed particle trapping and characterization chip, an array of microwires (as shown in FIG. 1B) can be defined by means of positive-tone photolithography, reactive ion etching, thermal evaporation of a 10 nm Cr, 40 nm Au bilayer and liftoff with an acetone soak assisted by low-power ultrasonication. The exemplary microwire design includes a contact pad for wire bonding interconnections to a custom-made chip carrier. On the exemplary microwires, the nanoelectrodes can be fabricated using an exemplary patterning scheme by electron beam overlapping and overexposure to create a small strip of e-beam resist between the exposed electrode tip regions due to the Gaussian nature of the electron beam. In the described example fabrication method, all features defined during this first step were written with the use of an Elionix ELS-7000 Ultra High Precision Electron Beam Lithography System, e.g., at 100 pA of emission current and an acceleration voltage of 100 kV. The substrates can be spin coated with a layer of PMMA A4 950 MW e-beam resist (e.g., from Microchem, Newton Mass.) and baked at 180° C. Following e-beam writing and development in MIBK:IPA solutions, a surface cleaning process, which includes a slow rate residual polymer descum for 1 min, can be performed with 18/2 sccm of Ar/O$_2$, 10 watt power and a pressure of 4 mtorr with the aid of a reactive ion etcher (e.g., such as RIE Plasmalab 80, Oxford Instruments).

Following the surface descum, an e-gun metal evaporation step can be performed (e.g., using an AST PEVA 600 E System (AST Instruments, Taiwan)). A 40 nm thin film of Ti can be deposited. The residual metal and e-beam resist mask can be lifted off in acetone and 2-propanol, a subsequent 10 min bath in a resist remover (e.g., 1165 remover (Microchem, Newton Mass.)), followed by a 1.5 min O$_2$ plasma clean to remove residues of the organic solutions.

In some implementations, the chip 100 can be structured to include multiple groups of nanogap electrode pair structures 150 having different sizes of nanogaps between the nanoelectrode tips 153 and/or different thicknesses of the nanoelectrode tips 153. In one example, the chip 100 includes three different groups having five electrode pairs to form 15 particle trapping structures. For example, within the groups of 5 wires, each gap includes a distinctive geometrical design.

Exemplary implementations using this exemplary configuration of the chip 100 were used to investigate the effect of tip geometry on the trapping of molecules and the enhancement of Raman scattering. For example, the internal angle of the electrode pairs were configured to be substantially 120° for the sub-10 nm gap.

The exemplary implementations included inspecting the chips using scanning electron microscopy (e.g., FEI Nova) at various magnifications, at acceleration voltage of 20 kV, UHR mode and a working distance of 5 mm before the beginning of the investigation, for example, to look for fabrication defects and confirm the quality of the gaps. Ohmic contact was inspected with a digital multimeter (e.g., 34411A, Agilent), and a typical resistance measured in air was in the order of $10^{11}$-$10^{12}\Omega$, e.g., indicating an excellent insulation of the underlying thermally grown SiO$_2$ layer and the absence of leakage currents between tips.

The exemplary implementations of DEP trapping and electronic detection were conducted using a custom-made printed circuit board with signal amplification, filtration and data acquisition capabilities. For example, different AC field conditions were applied, ranging from hundreds of kHz up to 4 MHz and various amplitudes from 0.1 to 10 Vp-p, coupled with a DC bias typically between 10 and 100 mV, in which the AC field is responsible for the DEP trapping, and the DC bias leads to the net current (~pA-nA) across the nanogaps. In the exemplary implementations, the AC field was applied by a function generator (e.g., 33220A, Agilent) and monitored by an oscilloscope. The exemplary particle analysis platform can be implemented for electronic detection of trapped molecules relying on the observation of tunneling current across the nanogaps. For example, such signals were retrieved through a transimpedance amplifier (TIA) with a low-pass filter as key component.

The exemplary implementations used R-phycoerythrin (RPE) as an exemplary particle for trapping using the exemplary particle analysis platform. For example, RPE is a 240 kDa disk-shaped protein with a diameter of 11 nm and a thickness of 6 nm derived from red algae 30. RPE is autofluorescent from the chromophore embedded in its molecular structure. RPE (e.g., 4.0 mg/mL, obtained from Thermo Scientific) was cassette dialyzed in PBS buffer (e.g., 100 mM Na$_2$HPO$_4$, 150 mM NaCl, pH 7.2), then diluted to 0.8, 0.26 and 0.12 nM final protein concentrations. Protein concentrations were determined using a spectrophotometer (e.g., Nanodrop, Thermo Scientific) from Beer's Law with extinction coefficient $2.0\times10^6$ L M$^{-1}$ cm$^{-1}$ at 567 nm. For further verification, a Bradford Microassay, calibrated against BSA, can also be used to determine the protein concentration.

For confocal Raman and fluorescence microscopy, a small fluidic chamber defined in a double-sided adhesive tape (70 μm thick) was used to encapsulate a 2 μL droplet of protein solution. For example, the chamber was sealed against evaporation by a circular coverslip of 5 mm diameter (Knittel Gläser) and vacuum-grade grease applied on the edges to keep the solution from evaporation. Raman spectra were obtained using a Horiba Labram 2 confocal Raman microscope with a HeNe laser (633 nm) as light source and 50×(N.A. 0.5) and 100×(N.A. 0.9) objectives (Olympus) where appropriate. The polarization of the incident light was along the axis defined by the direction of the electrode nanogaps. Spectral mapping used confocal point illumination by a laser spot whose dimensions are diffraction-limited. Spatial sampling density was defined using the Nyquist criterion. Time for sampling of one voxel was 1 s. Single-voxel, time-lapsed Raman spectra acquisition at the nanogap hotspot was also performed with 1 s exposure time. Fluorescence microscopy was also performed using an inverted fluorescence microscope (Leica DMI6000), with a xenon lamp as light source and a K3 filter cube (e.g., ex/em BP 470-490 nm/LP 515, Leica). A 100× oil-immersion objective (e.g., Leica, N.A. 1.4), and an EMCCD camera (e.g., IXon-888, Andor Technologies) using an exposure time of 25 ms/frame were used to make the observations.

The exemplary implementations included computational modeling of the nanogaps to analyze the distribution of electric fields at optical frequencies in the nanogaps. For example, the time-harmonic Maxwell equations were solved numerically using the finite element method (FEM)-based electromagnetic solver JCMsuit. The nanogap tips were modeled in a domain with cylindrical coordinates by creating a half-plane geometry of the tips and appropriate boundary condition applied along the rotational symmetry axis. Further detail of the nanogap modeling are described.

Figure 2A:
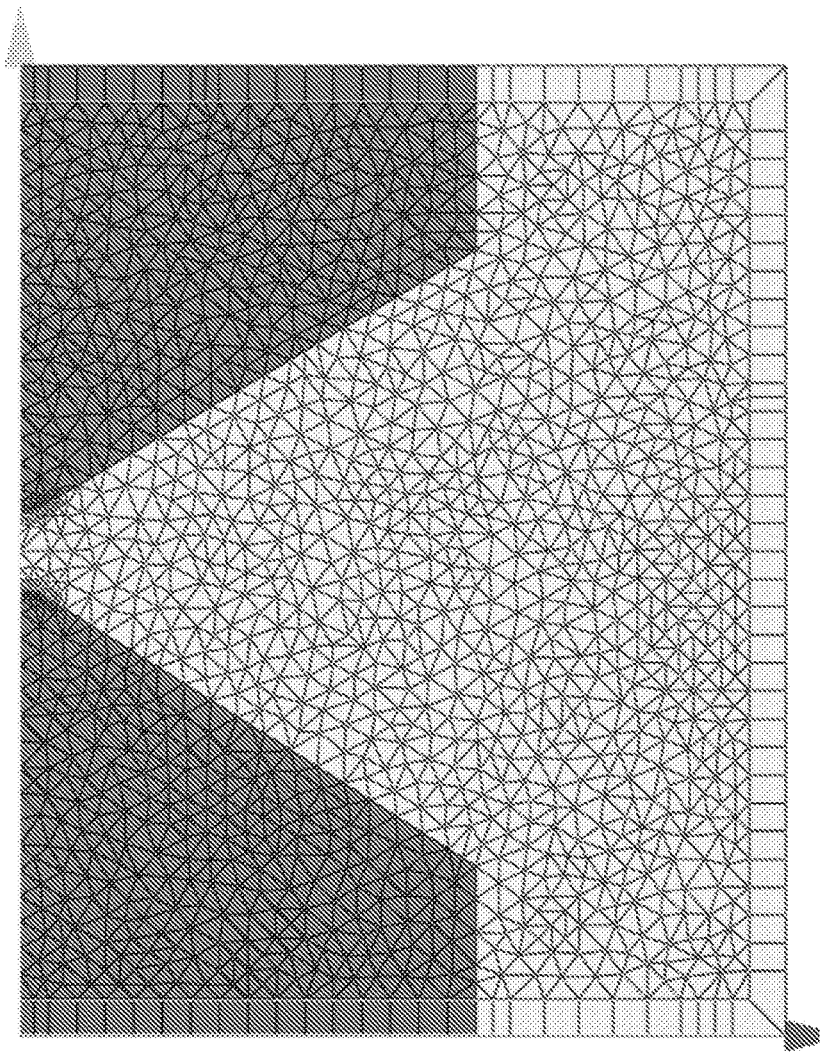
FIG. 2A shows a triangulated computational domain diagram of an exemplary nanoelectrode.

FIG. 2A shows a triangulated computational domain diagram of an exemplary nanoelectrode. The left axis of the diagram is the cylinder axis. For example, the complex refractive index of the metallic electrodes was set to 2.15325+2.9248i, corresponding to the value for titanium at 633 nm. The surrounding dielectric had a refractive index of 1.0. The radius of the tip was kept constant at 10 nm while tip angles were varied from 20-120°. This leads also to a variation in tip length. The gap between the tips can be varied from 5-20 nm in steps of 5 nm. In the exemplary cases, a source at 633 nm with the polarization along the direction defined by the tips impinges at the tips perpendicular to the tip axis with unit field strength.

Figures 2, 2B:
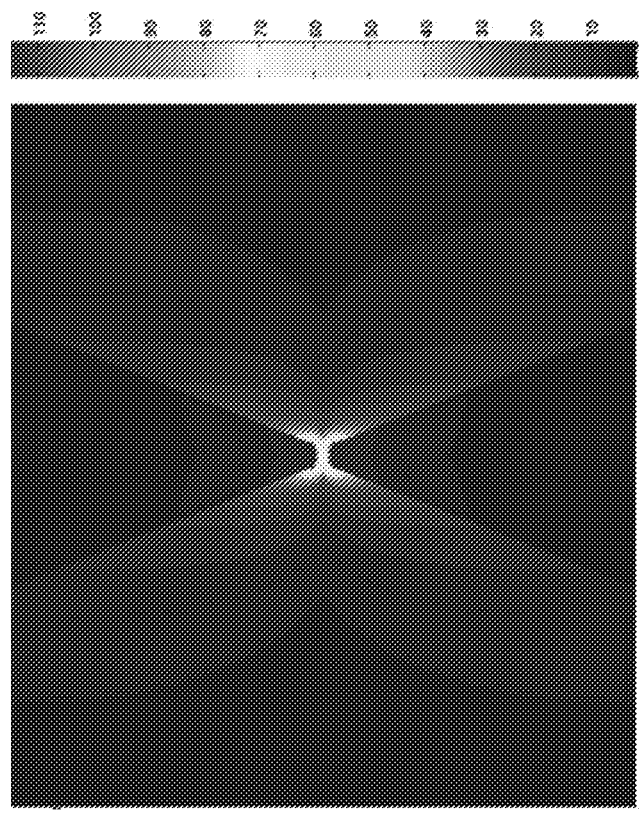
FIGS. 2B-1 and 2B-2 show distributions of modulus of electric field (|E|) of exemplary nanogaps.
Figures 1, 2B:
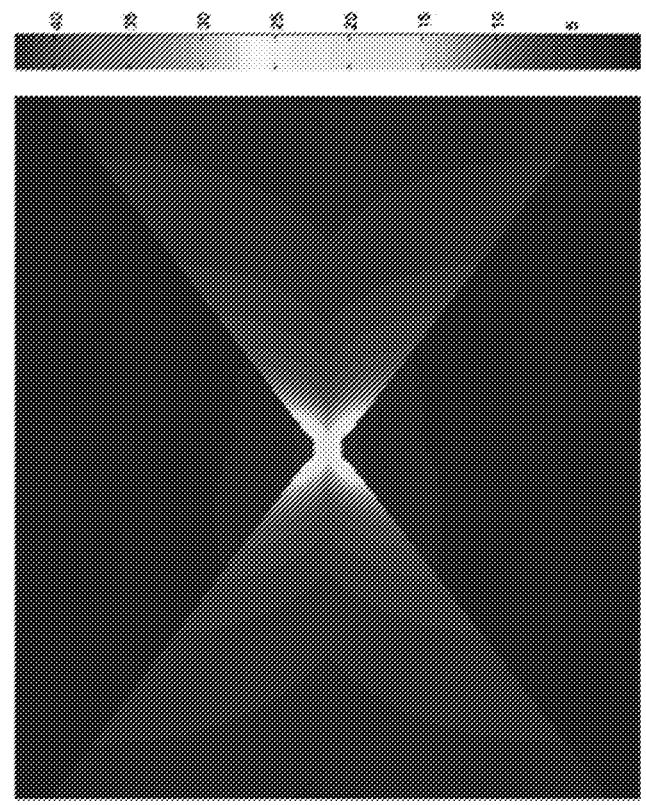

FIGS. 2B-1 and 2B-2 show distribution of modulus of electric field ($|E|$) diagrams at 633 nm around in a nanogap of 10 nm between Ti tips with an internal angle of 100 degrees (FIG. 2B-1) and a similar result for lower inner angle (40 degrees) in a nanogap of 5 nm (FIG. 2B-2). For example, in the exemplary 100° tip internal angle case with 10 nm spacing (FIG. 2B-1), the maximum value of $|E|^4$ is $1.6 \times 10^6$ in air, corresponding to $1.7 \times 10^5$ in aqueous buffer. This degree of electromagnetic enhancement was observed to show Raman signal of RPE in the exemplary implementations, and is sufficient to render single molecule sensitivity. Analyzing the exemplary simulation results for different tip angles showed the enhancement to increase for narrower tips, e.g., as shown by the tips with lower inner angle in FIG. 2B-2. For example, reducing the tip angle geometry to 40 degrees, $|E|^4 > 10^8$ can be predicted to be achieved. The exemplary model can be implemented to design nanogaps that will allow higher detection sensitivity along with improved trapping capabilities, as sharper electrode shapes render bigger nonuniformities of the electric field needed for DEP.

The level of field enhancement depends on the gap width. As the gap becomes smaller, $|E|$ increases. The exemplary simulation results are consistent with the observation that no Raman signal could be detected for gaps with larger gap size. It is noted, for example, that the shape and intensities predicted by this exemplary model do not take into account asperities of the metal material, as well as deformations in the shapes which are present in the real nanostructures, in particular when gaps are in the order of 4-5 nm. This kind of asperities might increase the value of the enhancement further, to the level sufficient for single molecule sensitivity. It also noted that the presence of an oxide layer on Ti was not taken into account in the exemplary model.

In the exemplary implementations, real-time Raman scans and electronic detection of the trapped protein molecules were performed. For the Raman spectroscopy, for example, the laser focus was positioned at a point of maximum Raman intensity which corresponds to the location of the nanogap. A region of high intensity was observed in an exemplary spectral map without baseline subtraction, e.g., including luminescence contributions of the Si phonon at 520 cm$^{-1}$, e.g., as shown in the image 170 of FIG. 1K. The high intensity region was observed in both dry and wet chip conditions.

Figure 3A:
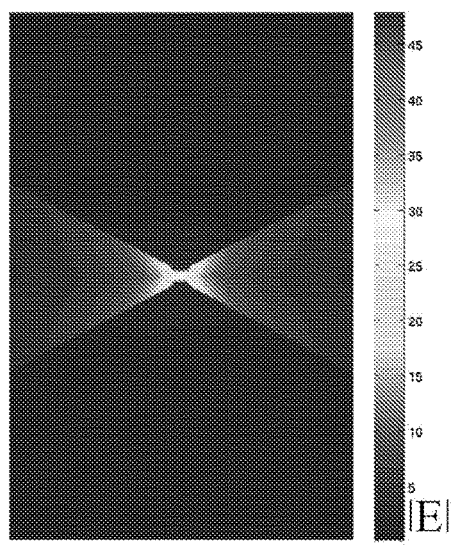
FIG. 3A shows a distribution of modulus of electric field (|E|) of an exemplary nanogap.

FIG. 3A shows a distribution of modulus of electric field ($|E|$) at 633 nm around in an exemplary nanogap of 5 nm between Ti tips with an internal angle of 120°. The values shown in FIG. 3A are multiples of the time-averaged amplitude of the source.

Figure 3B:
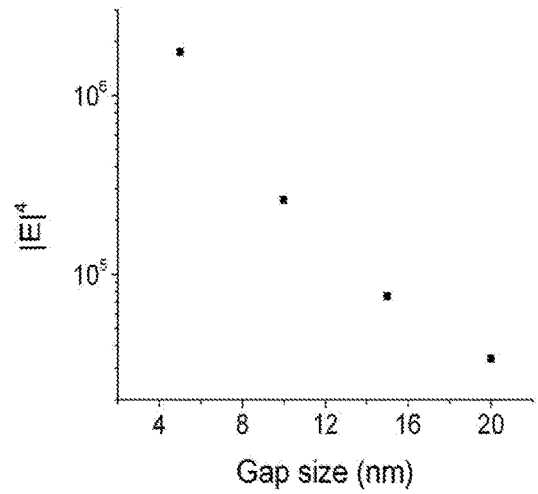
FIGS. 3B and 3C show a data plot of the SERS enhancement factor $|E|^4$ versus distance between exemplary tips and angle of the exemplary tip, respectively.
Figure 3C:
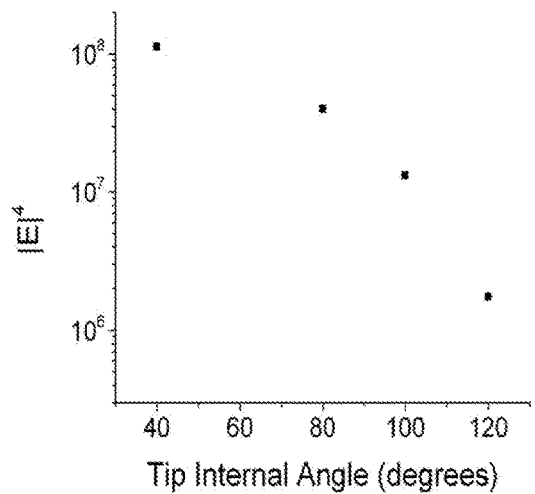

FIG. 3B shows a data plot of the SERS enhancement factor $|E|^4$ at point of maximum field enhancement vs. distance between tips, e.g., for 120° internal angle tip. FIG. 3C shows a data plot of the SERS enhancement factor $|E|^4$ at point of maximum field enhancement vs. angle of the tip, e.g., for 5 nm gap.

These exemplary Raman scans provided an indication of the location of the Raman hotspot on the chip. The same hotspot also provided enhancement of the Raman signal of molecules at place, which was demonstrated by introducing a drop of paraffin on the gap and sealing it with a cover slip, e.g., as shown in the image 175 of FIG. 1K. For example, the exemplary results of the FEM solutions of the Maxwell equations for the modulus $|E|$ of the electric field at 633 nm around the electrode nanogap validated this region of high electric field at the rim of the nanogap between the Ti metal tips.

Figure 3D:
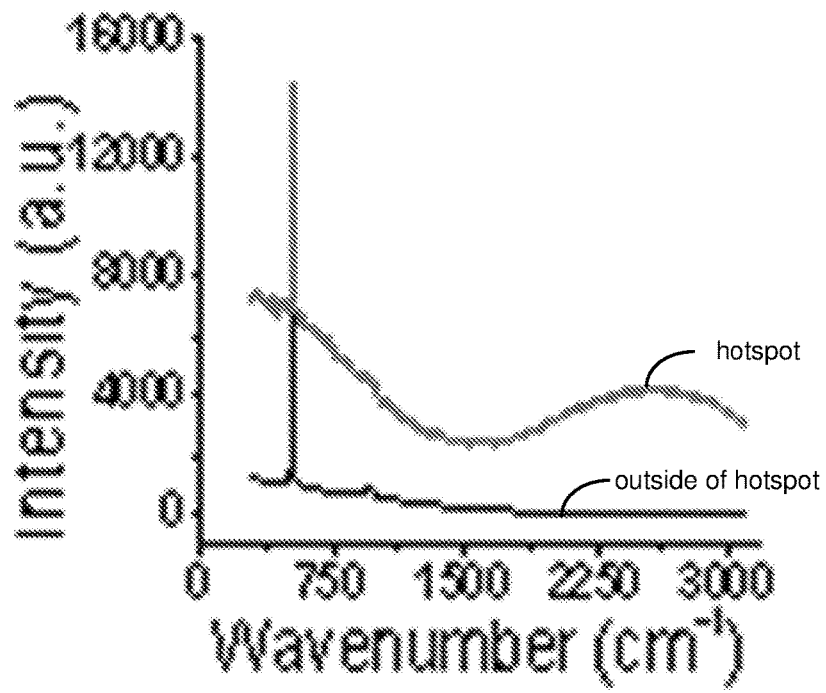
FIGS. 3D and 3E show Raman spectra plots of SERS hotspot on the exemplary microchip having the nanogap electrode array of the exemplary particle analysis platform.
Figure 3E:
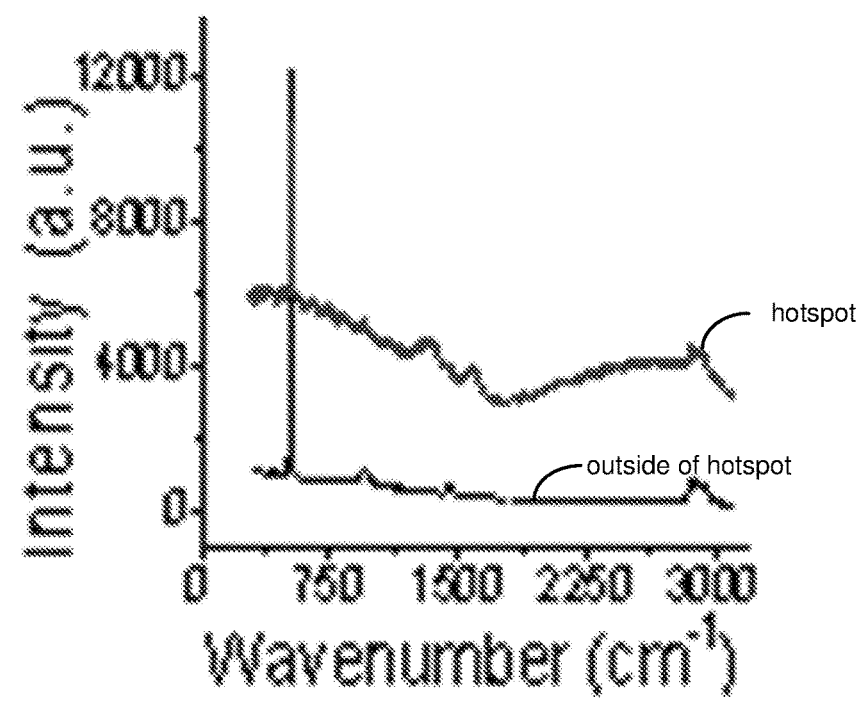

FIGS. 3D and 3E show spectra plots showing that the location of the "hotspot" of the baseline-enhanced region correspond to the position where the maximum intensity of the paraffin peaks occurs, e.g., when measuring with baseline correction. The spectra map of FIG. 3D shows the representative Raman spectra of an exemplary empty chip. The spectra map of FIG. 3E shows the representative Raman spectra of an exemplary paraffin sample in the hotspot, which features the typical CH stretching modes (2900-3000 cm$^{-1}$), CH$_2$ bending modes (1460 cm$^{-1}$), and the silicon phonon (520 cm$^{-1}$), and outside the hotspot.

Figure 4A:
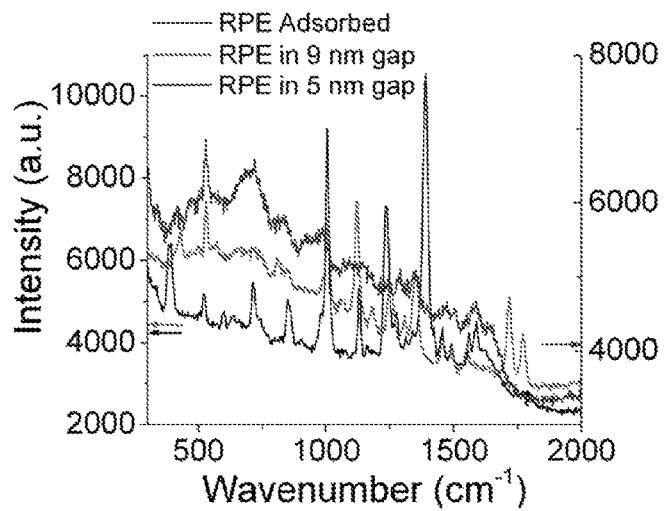
FIG. 4A shows a Raman spectra plot during an exemplary trapping event of particles in exemplary 5 nm and 9 nm nanogaps of the exemplary particle analysis platform.

For example, the located "hotspot" was used for subsequent point illumination, time-dependent and DEP assisted Raman measurements with RPE samples in solution during the exemplary implementations. FIG. 4A shows a Raman spectra plot of trapped RPE in a 5 nm and 9 nm gap compared against the RPE sample adsorbed in the hotspot of an exemplary Ag colloid hydrosol. The Raman spectra plot of FIG. 4A shows the match of most distinctive vibrational modes for the protein under SERS conditions. For example, the spectrum contains a number of bands which can be tentatively assigned to typical protein structural elements: peaks at 1650 cm$^{-1}$ (Amide I), 1585 cm$^{-1}$ (anti-symmetric stretching mode of side chain COO$^-$), 1470 cm$^{-1}$ (CH deformation mode of aliphatic CH), 1350/1290 cm$^{-1}$ (tentatively Amide III mode) and 820/720 cm$^{-1}$ (CH deformation mode in aromatic systems). Aromatic and COO$^-$-containing side chains are abundant in RPE. In the 9 nm gaps (e.g., gap distance~hydrodynamic diameter of RPE), the spectra strongly resembles the spectrum obtained after adsorption of RPE to Ag hydrosols, with several peaks in the range of the amide III modes. In 5 nm gaps, the intensity is considerably lower, as only protein chains can penetrate the gap.

Figure 4B:
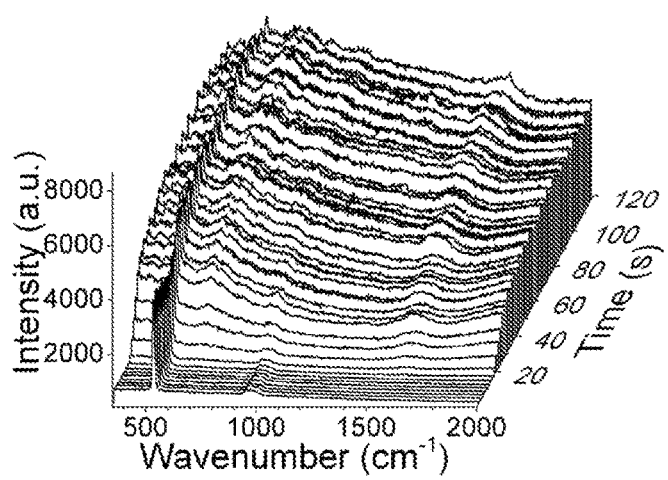
FIG. 4B shows another Raman spectra plot during the exemplary trapping event.

FIG. 4B shows a spectra plot of the time-dependent Raman spectra during an exemplary trapping event. For example, the spectra plot shows the time evolution of Raman spectra obtained from the exemplary 5 nm nanogap hotspot, in which the RPE concentration was 0.8 nM in 1×PBS buffer, the DC bias signal was 0.1 V, and the AC signal was 7 $V_{P-P}$, 1 MHz. In the first few seconds after switching the field to DEP trapping conditions, just the typical silicon substrate spectrum was observed. Between 10 and 20 s after the start, a number of narrow Raman peaks appeared on top of the fluorescence background, e.g., indicating the molecular Raman signature becomes more pronounced in the course of the implementation.

Figure 4C:
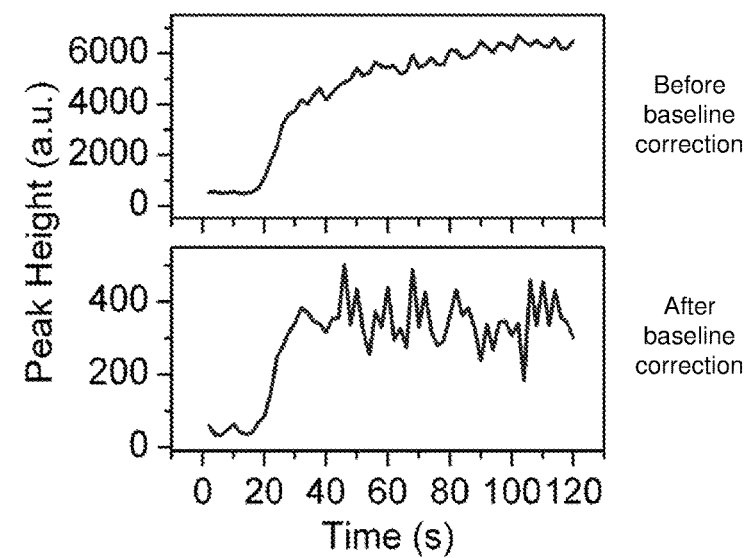
FIG. 4C shows exemplary data plots of the peak height at 720 $cm^{-1}$.

FIG. 4C shows data plots showing the time evolution of the peak height at 720 cm$^{-1}$ before and after the baseline correction. For example, the increase in Raman and luminescence intensity demonstrates that the increasing number of protein molecules in the vicinity of the gap were trapped to the nanogap, and may have eventually reached saturation.

Figure 4D:
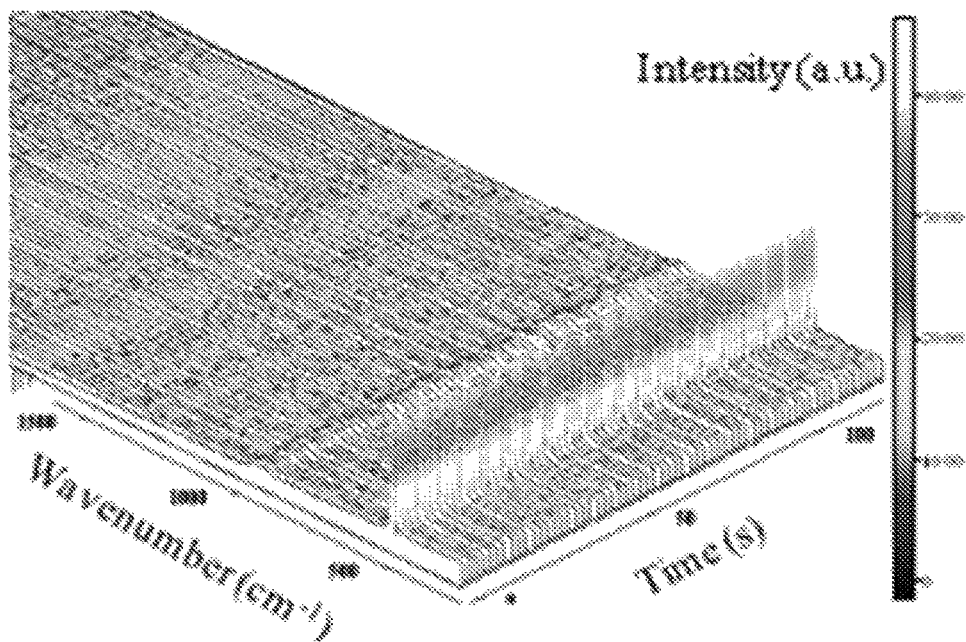
FIG. 4D shows an exemplary non-trapping Raman spectra plot.

FIG. 4D shows a spectra plot of the time-dependent Raman spectra obtained from the exemplary 5 nm nanogap hotspot during a non-trapping event in 1×PBS buffer. For example, the exemplary spectra plot can be used as an exemplary Raman signature plot representing the absence of particles trapped. For example, the exemplary conditions include a DC bias signal of 0.1 V and an AC signal of 7 $V_{P-P}$, 1 MHz.

Figure 4E:
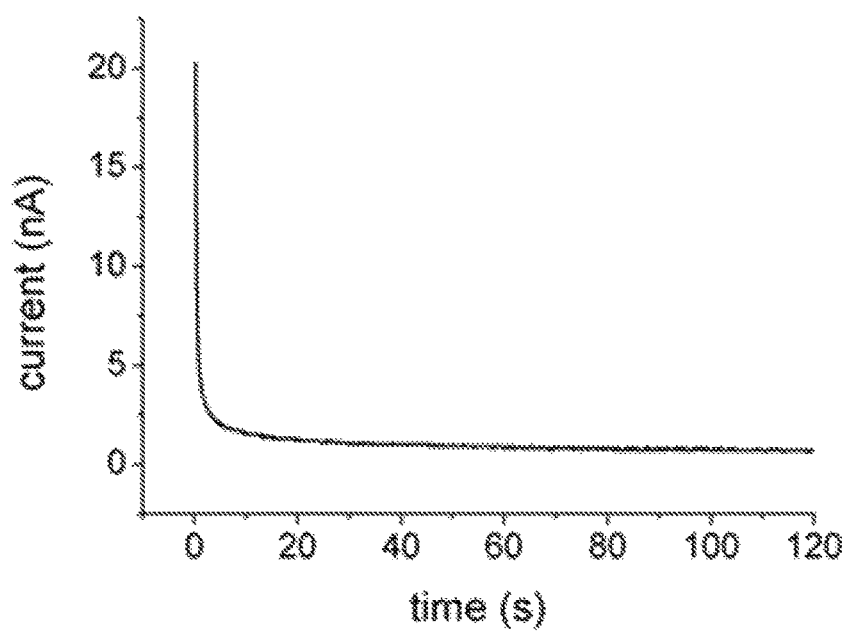
FIG. 4E shows an exemplary non-trapping current versus time plot.

In addition to the Raman measurements, electronic measurements were also performed. FIG. 4E shows a current versus time data plot exemplifying the electronic signature during the non-trapping event of particles across the exemplary 5 nm nanogap under similar conditions as in FIG. 4D. For example, this was observed when just the DC detection bias is applied to the solution containing molecules, or when the AC frequencies applied were far from the ones leading to trapping. The shape of the exemplary current-time curve may indicate a capacitive current, e.g., the charging curve of a capacitor, which would mean the polarization of the solution. For example, the curve reaches a stable base condition, e.g., which can be attributed to ionic current flow. While a DC bias might contribute to the trapping of molecules by means of electrostatic trapping, it is in orders of magnitude higher than the substantially lower voltage (e.g., tens of millivolts) applied in the disclosed particle analysis platform. For example, this provides a reason why there are no observable changes in the current measurement when the DC bias alone was applied. For example, superimposing high-frequency modulation on the applied bias with a much larger amplitude minimizes electrochemical effects on the electrodes and accounts mainly for DEP-related trapping phenomena.

Figure 5A:
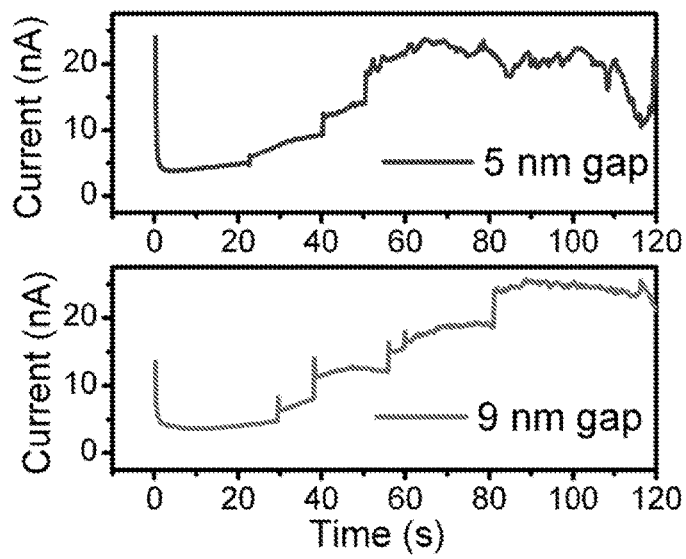
FIG. 5A shows current versus time data plots during an exemplary trapping event of particles in exemplary 5 nm and 9 nm nanogaps of the exemplary particle analysis platform.

FIG. 5A shows current versus time data plots exemplifying electronic signatures of RPE molecules trapped by DEP across an exemplary 5 nm nanogap (top plot) and an exemplary 9 nm nanogap (bottom plot). For example, the conditions of the exemplary implementation to generate the data plots included an RPE concentration of 0.8 nM in 1×PBS buffer, a DC bias signal of 0.1 V, and an AC signal of 6 $V_{P-P}$, 1 MHz. As shown in the figure, when the exemplary DEP conditions are applied, an increase in tunneling current is observed for both 5 and 9 nm gaps, e.g., relating to protein molecules bridging the gap, and thus allowing the tunneling current to flow through the junction. It is noted there are distinctive features of the electronic signals observed. For example, the current jumps in a stepwise manner, which can suggest that the trapping of RPE may occur on a molecule-by-molecule basis, e.g., due to the limited number of protein molecules in the vicinity of the trap where the DEP force exceeds the thermal drag force or threshold force, which is defined from the diffusion path during the implementation. For example, for the 0.8 nM RPE concentration, there is on average 1 protein molecule per every 2.0 μm$^3$, 0.26 nM (e.g., 1 molecule per 6.12 μm$^3$) and 0.12 nM (e.g., 1 molecule per 12.75 μm$^3$).

Figure 5B:
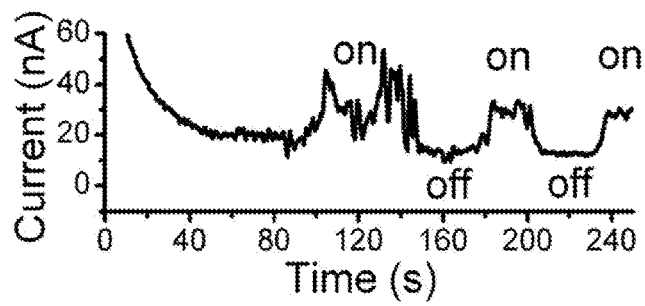
FIG. 5B shows an exemplary current versus time data plot showing on-off-on switching of the AC signal.

FIG. 5B shows a current versus time data plot showing on-off-on switching of the AC signal during the acquisition for the 0.12 nM solution across the exemplary 5 nm nanogap, indicating the reversibility of the trapping process, e.g., with a typical current difference from 15 to 25 nA between the trapping and non-trapping conditions.

Figure 5C:
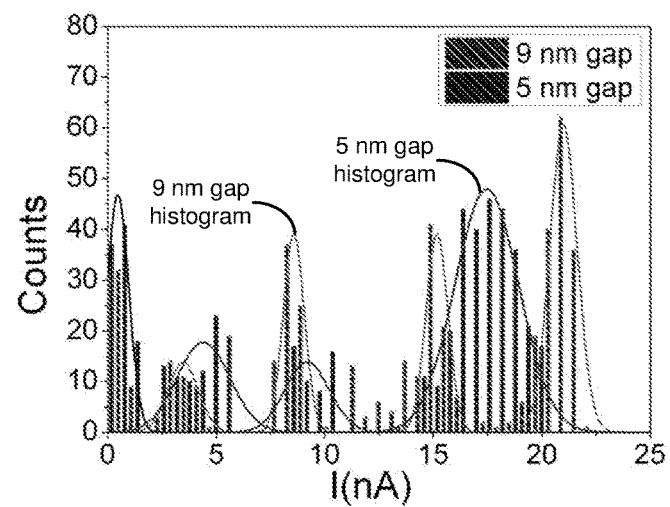
FIG. 5C shows histograms from the exemplary molecular trapping tunneling current data.

FIG. 5C shows a histogram including tunneling current histograms of 0.8 nM RPE from trapping data in exemplary 5 nm nanogaps (blue) and exemplary 9 nm nanogaps (red), corresponding to the distribution of individual current increases or jumps. For example, the discrete distribution of tunneling current measurement can demonstrate the bridging of an RPE molecule on a molecule-by-molecule fashion as trapped in the gap by DEP force. The exemplary histograms were constructed with the recorded data for the 0.8 nM concentration case for both the 5 and 9 nm gaps, which reveal at least three distinctive distributions with well-defined peaks that indicate the complete or partial contact of RPE molecules as they bridge the nanogap, thus allowing the current to increase. For example, at least three RPE molecules are estimated to have been trapped in the 5 nm gap, and the possibility of four molecules bridging the gap clearly exists based on the number of frequency counts in the 9 nm gap, as shown in FIG. 5C.

The exemplary tunneling current histograms of FIG. 5C were constructed with the $I_{5nm}$ and $I_{9nm}$ traces using Origin data plot software. Background current was subtracted from I values to extract the current increase. Based on the resulting statistics, frequency count peaks were found and a fit algorithm was used to fit the multiple peaks in the data. The resulting distribution curves were overlaid to the existing histogram by adding a new Y axis on the right side and linking the axis scales. The exemplary lines are fitted to the pronounced peaks at 0 A that originate from the base level current (e.g., 3.7-4.1 nA) at which the ionic current reaches stability after its initial decrease and before the onset of trapping.

For example, the highest value of the field gradient $\nabla E^2$ is expected in the inter-electrode space where molecular trapping was observed (e.g., ~1.5×10$^{18}$ V$^2$/m$^3$ for the smaller nanogaps in the array). It is noted, for example, the space where the dielectrophoretic force exceeds molecular diffusion can extend to a large volume above the surface of the device. Also it is noted, for example, that the EDL overlapping in the nanogap case-scenario is excluded in the high conductivity buffers, but it could be occurring in low conductivity buffers [e.g., 10 µS/cm and below] and contribute to prolonged time for the onset of trapping. However, this could be a reality in the beginning, but as ion separation effects take place upon the application of the DC detection bias signal (e.g., the current decrease observed at beginning of the curve in FIG. 5A), this might facilitate the AC trapping mechanism after the base ionic conduction is reached.

For example, differences in the time evolution between Raman data and electronic (tunneling current) data can be understood from the different detection mechanisms. Tunneling current measurements sensitively require the molecule to be in a position to bridge the gap between the metal electrodes for a signal change, while the Raman signal shows a gradual increase when the protein molecules approach the gap. Further, the point of maximum sensitivity for the Raman detection is slightly outside the gap, exemplified by FEM simulations of FIGS. 2B-1 and 2B-2. Thus, for example, the stepwise manner of trapping is not readily visible in the Raman signal.

Figure 6A:
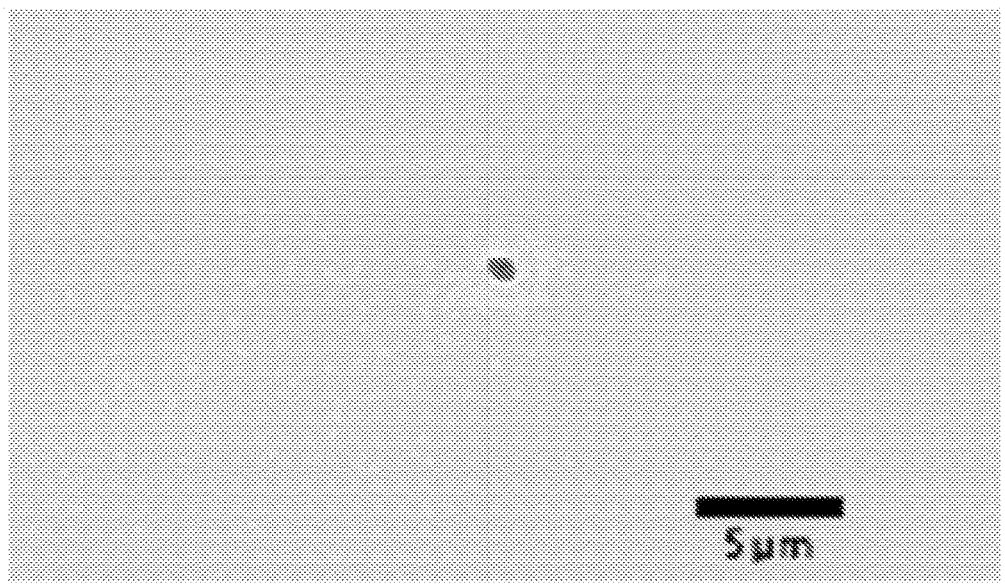
FIG. 6A shows an exemplary fluorescence image of molecules trapped in an exemplary 9 nm electrode nanogap.

As RPE is an intrinsically fluorescent protein, fluorescence microscopy during trapping was performed to further verify the presence of the molecules. FIG. 6A shows a fluorescence image of RPE molecules trapped in an exemplary 9 nm electrode nanogap after 30 s of the applied DEP field, e.g., in which the conditions include 0.8 nM RPE concentration, an AC signal of 6 $V_{P-P}$, 1 MHz, and a DC bias signal of 0.01 V, with 24 µM PBS concentration and 15 µS/cm conductivity. For example, as the local concentration increases, so does the fluorescence intensity. Fluorescence intensity originates from a spot region of 0.9 µm diameter around the nanoelectrode.

Figure 6B:
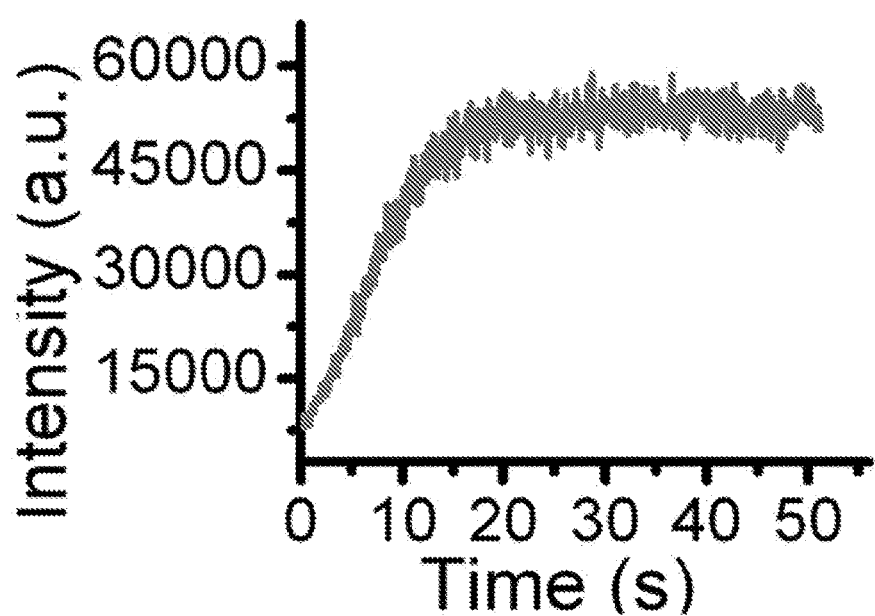
FIG. 6B shows an exemplary data plot of fluorescence intensity after photobleaching correction as function of time.

FIG. 6B shows a data plot of fluorescence intensity after photobleaching correction as function of time, e.g., where t=0 corresponds to the onset of trapping event. For example, the intensity builds up as molecules get attracted to the trap, and the intensity value reaches a constant value after the initial 20 s of applying the electric field.

Exemplary current versus time electronic and fluorescence signatures were acquired simultaneously during trapping events for exemplary particles employed in the system at a lower protein concentration (e.g., 0.12 nM), which can be characteristic of single molecule detection.

Figure 6C:
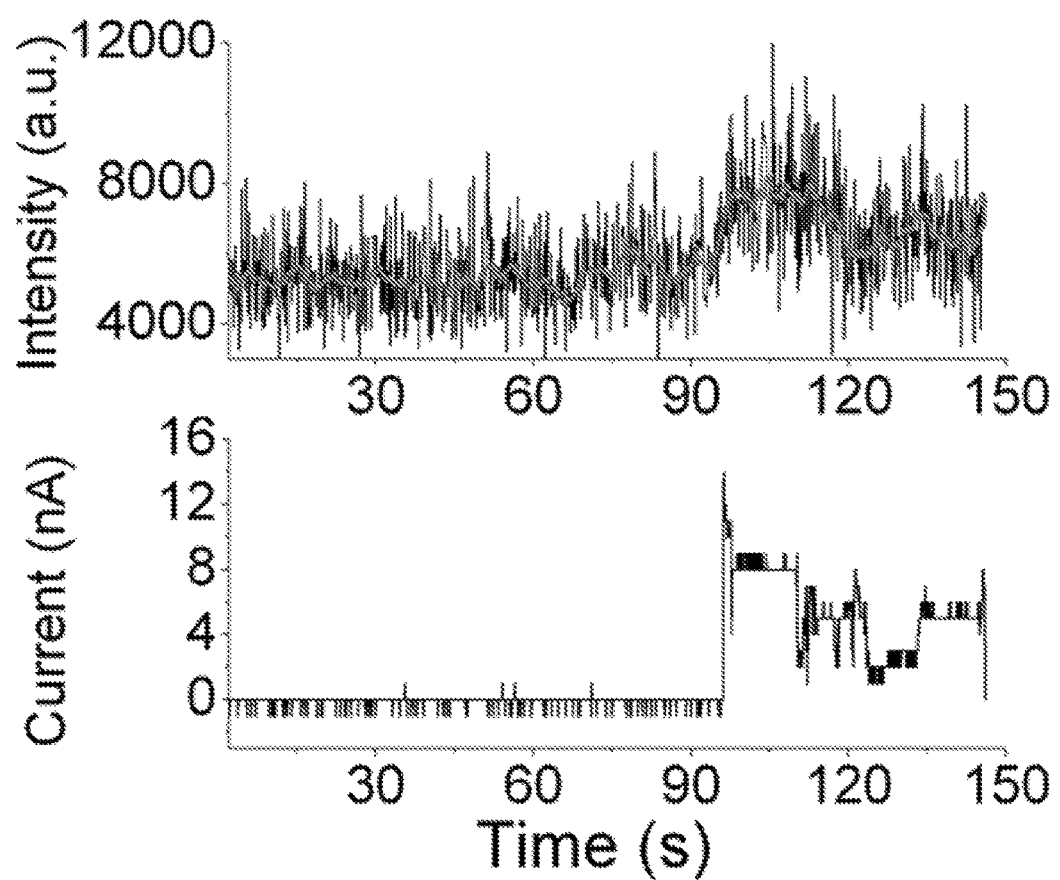
FIG. 6C shows a fluorescence intensity versus time data plot and a current versus time data plot for an exemplary trapping event using a lower protein concentration.

FIG. 6C shows a fluorescence intensity versus time data plot and a current versus time data plot for an exemplary trapping event using a lower protein concentration than that used in the exemplary implementations described in FIGS. 5A-5C. In FIG. 6C, the top plot shows the fluorescence intensity after photobleaching correction vs. a time trace, and the bottom plot shows the inter-electrode current vs. time, in which the conditions for the exemplary implementation included a 0.12 nM RPE concentration, an AC signal of 1-10 $V_{peak-to-peak}$, 1 MHz, a DC bias signal of 0.01 V, with a 3.6 µM PBS buffer concentration and 4 µS/cm conductivity. As shown in the figure, there is a sigmoidal increase of the fluorescence intensity in accordance with the previous observations, however the final intensity value is smaller. The current versus time electronic signature was obtained in parallel during the same trapping event. The onset of DEP is observed for both cases after 90 s. Both fluorescence and current increase simultaneously at the beginning, and subsequently fluctuate simultaneously. The value of current is smaller compared to the one detected with higher protein concentrations, in accordance with the observed lower fluorescence and the statistical data. For example, as shown in the current vs. time data plot, a single current jump is demonstrated that may be characteristic of single molecule detection.

The exemplary implementations described herein demonstrate the disclosed real-time analytical methods, systems and devices for particle capturing, manipulation and interrogation. For example, the exemplary system embodiment involving a well-patterned sub-10 nm electrodes nanogap array was shown to actively transport and trap proteins through DEP, which then enabled the electronic (e.g., tunneling current) and Raman spectroscopic detection of the trapped molecules. The exemplary chip and electronic detection technology can be easily mass produced with high yield and coupled to widely-used spectroscopic instruments. The disclosed platform demonstrated a practical way for low-copy number protein detection which may be applied in a variety of applications for low-concentration heterogeneous sample analysis at the single/few molecule level.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A device to capture and characterize particles in a fluid by combining sensing via electrical tunneling and coherent optical Raman sensing, comprising:
   a substrate that is electrically insulating;
   a channel formed of an electrically insulative material on the substrate and structured to carry an electrically conducting fluid containing particles;
   a first electrode and a second electrode formed of an electrically conductive material and located in the channel to form an opening with a size in the nanometer range, each of the first and second electrodes structured to include a tip having an angle from 20 degrees to 120 degrees and including an electrically insulating layer over the electrode surface including at the opening between the electrodes;
   a first circuit electrically coupled to the first and second electrodes to apply a non-uniform AC electric field and a DC bias signal across the first and second electrodes, wherein the applied non-uniform AC electric field produces a positive dielectrophoretic force ($F_{PDEP}$) in a direction towards the opening to capture a low quantity of the particles including 1,000 particles or fewer in a trapping region including the opening and in a region adjacent to the opening;

a second circuit coupled to the first and second electrodes to detect changes in a DC current produced by electrical tunneling through the opening and the electrically insulating layers over the electrode surfaces of the first and second electrodes based on operation of the applied DC bias signal and caused by at least some of the captured particles in the trapping region due to operation of the first circuit; and an optical device including a laser to direct a coherent light beam on the opening and including a detector to detect inelastic scattering of the light beam by at least some of the captured particles in the trapping region due to operation of the first circuit to determine their Raman spectra.

2. The device as in claim 1, wherein the first and second electrodes are structured to extend into the channel such that the electrodes narrow a channel dimension.

3. The device as in claim 1, wherein the electrically insulative material includes at least one of glass, silica, oxidized silicon, silicon nitride, polysilsesquioxane (PSQ), polymethylmethacrylate (PMMA), or plastic.

4. The device as in claim 1, wherein the particles include at least one of proteins, nucleic acids, peptides, carbohydrates, or nanoparticles.

5. The device as in claim 1, wherein the size of the opening is in a range of 1 to 10 nanometers.

6. The device as in claim 1, wherein the electrically insulating layer includes a native metal oxide coating.

7. The device as in claim 6, wherein the native metal oxide coating includes titanium oxide.

8. The device as in claim 7, wherein the titanium oxide coating is configured to have a thickness of 0.1 to 2 nanometers.

9. The device as in claim 1, wherein the electrically insulating layer is formed of a self-assembled monolayer.

10. The device as in claim 1, wherein the optical device is configured to detect an illumination intensity of the aggregated particles.

11. The device as in claim 10, wherein the illumination intensity includes a fluorescence intensity.

12. The device as in claim 1, further comprising a sensor located along the channel to detect a parameter of the captured particles, the sensor including at least one of an electrical sensor, an electrochemical sensor, a mechanical sensor, or a magnetic sensor.

13. The device as in claim 1, wherein the second circuit includes a transimpedance amplifier.

14. A method to capture and characterize particles in a fluid k combining electrical sensing via electrical tunneling and optical sensing via coherent optical Raman spectroscopy, comprising:

receiving an electrically conducting fluid containing particles in a channel formed of an electrically insulative material and having a pair of electrodes to form an opening at an interface between the electrodes with a size in the nanometer range, wherein the electrodes are structured to include a tip having an angle from 20 degrees to 120 degrees and an electrically insulating layer over the electrode surface at the opening;

selecting a frequency and magnitude of an AC electric field and a bias magnitude of a DC electrical signal to be applied across the electrodes;

trapping a low quantity of the particles including 1,000 particles or fewer by applying the AC electric field to capture the particles in a trapping region including the opening and in a region adjacent to the opening;

detecting the captured particles by applying the DC electric signal across the electrodes to measure a current produced based on the presence of the particles in the trapping region via electrical tunneling through the opening and the electrically insulating layers over the electrode surfaces of the pair of electrodes;

directing a coherent light beam at the opening;

detecting, using an optical device including a detector, inelastic scattering of the light beam by at least some of the particles captured in the trapping region;

determining Raman spectra from the detected light; and combining electrical sensing via the current based on electrical tunneling and optical sensing via the determined Raman spectra to measure the captured particles in the opening.

15. The method as in claim 14, wherein the applied non-uniform AC electric field produces a positive dielectrophoretic force ($F_{PDEP}$) in a direction towards the opening to capture the particles in the trapping region.

16. The method as in claim 14, wherein the particles include a first type of particles and a second type of particles.

17. The method as in claim 16, further comprising selecting electrical parameters to separate the first type of particles from the second type of particles based on differences in polarizability and electrokinetic mobility of the first and second type of particles.

18. The method as in claim 17, further comprising controlling the duration of the applied AC electric field to temporally control the separation of the first and second type of particles.

19. The method as in claim 14, wherein the particles include at least one of proteins, nucleic acids, peptides, carbohydrates, or nanoparticles.

20. The method as in claim 14, wherein the size of the opening is in a range of 1 to 10 nanometers.

21. The method as in claim 14, wherein the electrically insulating layer includes a native metal oxide coating.

22. The method as in claim 21 wherein the native metal oxide coating includes titanium oxide and is configured to have a thickness of 0.1 to 2 nanometers.

23. The method as in claim 14, wherein the electrically insulating layer is formed of a self-assembled monolayer.

24. A method to capture and characterize particles in a fluid by combining electrical sensing via electrical tunneling and optical sensing via coherent optical Raman spectroscopy, comprising:

receiving an electrically conducting fluid containing particles in a channel formed of an electrically insulative material and having a pair of electrodes to form an opening at an interface between the electrodes with a size in the nanometer range, wherein the electrodes are structured to include a tip having an angle from 20 degrees to 120 degrees and an electrically insulating layer over the electrode surface at the opening;

selecting a frequency and magnitude of an AC electric field to be applied across the electrodes;

trapping a low quantity of the particles including 1,000 particles or fewer by applying the AC electric field to capture the particles in a trapping region including the opening and in a region adjacent to the opening;

selecting a bias magnitude of a DC electrical signal to be applied across the electrodes;

detecting the captured particles by applying the DC electrical signal across the electrodes to measure a current produced based on the presence of the particles in the trapping region via electrical tunneling through the opening and the electrically insulating layers over the electrode surfaces of the pair of electrodes;

directing a coherent light beam on the opening;

detecting, using an optical device including a detector, inelastic scattering of the light beam by at least some of the particles captured in the trapping region; and determining a Raman spectra from the detected light.

25. The method as in claim 24, wherein the applied non-uniform AC electric field produces a positive dielectrophoretic force ($F_{PDEP}$) in a direction towards the opening to capture the particles in the trapping region.

26. The method as in claim 24, wherein the particles include a first type of particles and a second type of particles.

27. The method as in claim 26, further comprising selecting electrical parameters to separate the first type of particles from the second type of particles based on differences in polarizability and electrokinetic mobility of the first and second type of particles.

28. The method as in claim 27, further comprising controlling the duration of the applied AC electric field to temporally control the separation of the first and second type of particles.

29. The method as in claim 24, wherein the particles include at least one of proteins, nucleic acids, peptides, carbohydrates, or nanoparticles.

30. The method as in claim 24, wherein the size of the opening is in a range of 1 to 10 nanometers.

31. The method as in claim 24, wherein the electrically insulating layer includes a native metal oxide coating.

32. The method as in claim 31 wherein the metal oxide coating includes titanium oxide and is configured to have a thickness of 0.1 to 2 nanometers.

33. A system to characterize particles by combining electrical sensing via electrical tunneling and optical sensing via coherent optical Raman spectroscopy, comprising:

an electrode dielectrophoresis chip, including:
  (i) a substrate that is electrically insulating and structured to define a channel to carry an electrically conducting fluid containing particles, and
  (ii) an array of paired electrodes formed of an electrically conductive material and located in the channel to form an opening with a size in the nanometer range, wherein electrodes in at least one electrode pair of the array are structured to include a tip having an angle from 20 degrees to 120 degrees and an electrically insulating layer over the electrode surface at the opening;

an electrical energy source electrically coupled to the electrode dielectrophoresis chip to generate a non-uniform AC electric field and a DC bias signal across the paired electrodes, wherein the non-uniform AC electric field produces a positive dielectrophoretic force ($F_{PDEP}$) in a direction towards the opening to capture a low quantity of the particles including 1,000 particles or fewer in a trapping region including the opening and in a region adjacent to the opening;

a circuit board including an electrical circuit coupled to the first and second electrodes and configured to detect changes in a DC current produced by the applied DC bias signal caused by at least some of the particles captured in the trapping region via electrical tunneling through the opening and the electrically insulating layers over the electrode surfaces of the electrodes, the circuit board providing a base to attach the electrode dielectrophoresis chip and electrically couple the electrode dielectrophoresis chip to the electrical circuit;

an optical device including a laser to direct a coherent light beam on the opening and including a detector to detect inelastic scattering of the light beam by at least some of the particles captured in the trapping region; and a processing unit to process at least one of the detected light to determine their Raman spectra or the detected DC current as data to determine a characteristic of the particles.

34. The system as in claim 33, wherein the processing unit is configured on the circuit board.

35. The system as in claim 34, wherein the circuit board further includes a memory unit coupled to the processing unit to store the data.

36. The system as in claim 33, wherein the circuit board further includes an input/output unit to send at least one of the data, the detected DC current signals, or the Raman spectra data.

* * * * *